(12) United States Patent
Antonetti et al.

(10) Patent No.: US 7,585,865 B2
(45) Date of Patent: Sep. 8, 2009

(54) PROTEIN KINASE C ZETA INHIBITION TO TREAT VASCULAR PERMEABILITY

(75) Inventors: David A. Antonetti, Elizabethtown, PA (US); Jeffrey M. Sundstrom, Hershey, PA (US); Charles D. Smith, Mount Pleasant, SC (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 11/781,498

(22) Filed: Jul. 23, 2007

(65) Prior Publication Data

US 2008/0021036 A1 Jan. 24, 2008

Related U.S. Application Data

(60) Provisional application No. 60/832,362, filed on Jul. 21, 2006.

(51) Int. Cl.
*A61K 31/497* (2006.01)
*A61K 31/38* (2006.01)
*A61K 31/35* (2006.01)

(52) U.S. Cl. .................. 514/252.13; 514/438; 514/444; 514/460

(58) Field of Classification Search ............ 514/252.13, 514/438, 444, 460
See application file for complete search history.

(56) References Cited

U.S. PATENT DOCUMENTS

| 4,814,470 A | 3/1989 | Colin et al. |
| 4,829,081 A | 5/1989 | Damon, II et al. |

FOREIGN PATENT DOCUMENTS

| WO | WO-9320101 | 10/1993 |
| WO | WO-9916465 | 4/1999 |

OTHER PUBLICATIONS

National Heart, Lung and Blood Institute, Diseases and Conditions Index (Coronary Microvascular Disease), 2007.*
Harhaj, N.S., E.A. Felinski, E.B. Wolpert, J.M. Sundstrom, T.W. Gardner, and D.A. Antonetti. "VEGF Activation of Protein Kinase C Stimulates Occludin Phosphorylation and Contributes to Endothelial Permeability." *Investigative Ophthalmology & Visual Science* 2006, vol. 47, No. 11, pp. 5106-5115.
Parker, P.J. and J. Murray-Rust. "PKC at a glance." *Journal of Cell Science* 2004, vol. 117, pp. 131-132.
Dempsey, E.C., A.C. Newton, D. Mochly-Rosen, A.P. Fields, M.E. Reyland, P.A. Insel, and R.O. Messing. "Protein kinase C isozymes and the regulation of diverse cell responses." *American Journal of Physiology, Lung Cellular and Molecular Physiology* 2000, vol. 279, pp. L429-L438.
Antonetti, D.A., A.J. Barber, L.A. Hollinger, E.B. Wolpert, and T.W. Gardner. "Vascular Endothelial Growth Factor Induces Rapid Phosphorylation of Tight Junction Proteins Occludin and Zonula Occluden 1." *The Journal of Biological Chemistry* 1999, vol. 274, No. 33, pp. 23463-23467.
Antonetti, D.A., A.J. Barber, S. Khin, E. Lieth, J.M. Tarbell, T.W. Gardner, and the Penn State Retina Research Group. "Vascular Permeability in Experimental Diabetes Is Associated With Reduced Endothelial Occludin Content." *Diabetes* 1998, vol. 47, pp. 1953-1959.
Folgueira, L., J.A. McElhinny, G.D. Bren, W.S. MacMorran, M.T. Diaz-Meco, J. Moscat, and C.V. Paya. "Protein Kinase C-ζ Mediates NF-κB Activation in Human Immunodeficiency Virus-Infected Monocytes." *Journal of Virology* 1996, vol. 70, No. 1, pp. 223-231.
Stamatovic, S.M., O.B. Dimitrijevic, R.F. Keep, and A.V. Andjelkovic. "Protein Kinase Cα-RhoA Cross-talk in CCL2-induced Alterations in Brain Endothelial Permeability." *The Journal of Biological Chemistry* 2006, vol. 281, No. 13, pp. 8379-8388.
Kochs, G., R. Hummerl, D. Meyer, H. Hug, D. Marme, and T.F. Sarre. "Activation and substrate specificity of the human protein kinase C α and ζ isoenzymes." *European Journal of Biochemistry* 1993, vol. 216, pp. 597-606.
Coppola, G.M., R.E. Damon, and H. Yu. "Synthesis of Highly Functionalized Thiophenes. 4-Aryl-3-carboxylate Derivatives." *Synlett* 1995, pp. 1143-1144.
Soler, A.P., R.D. Miller, K.V. Laughlin, N.Z. Carp, D.M. Klurfeld, and J.M. Mullin. "Increased tight junctional permeability is associated with the development of colon cancer." *Carcinogenesis* 1999. vol. 20, No. 8, pp. 1425-1431.
Phillipson, A. et al., Protein kinase C-ζ inhibition exerts cardioprotective effects in ischemia-reperfusion injury, *American Journal of Physiology Heart and Circulatory Physiology*, vol. 289: H898-H907, 2005.

* cited by examiner

*Primary Examiner*—Kevin E Weddington
(74) *Attorney, Agent, or Firm*—Gifford, Krass, Sprinkle, Anderson & Citkowski, P.C.

(57) ABSTRACT

Methods of treating or preventing a disease or disorder in a subject are provided by the present invention which include administering a composition including a therapeutically effective amount of a protein kinase C (PKC) zeta inhibitor. A disease or disorder treated or prevented by administration of a PKC zeta inhibitor is characterized by abnormal vascular permeability. Diseases or disorders treated or prevented by administration of a composition including a therapeutically effective amount of a PKC zeta inhibitor include cancer, an ischemic condition and microvascular complications of a systemic or local condition in the subject, such as diabetes and/or diabetic macular edema. Additionally, methods of inhibiting PKC zeta are provided which include incubating PKC zeta in vivo, in vitro and/or in silico with a PKC zeta inhibitor.

1 Claim, 6 Drawing Sheets

PROTEIN KINASE C ZETA INHIBITION TO TREAT VASCULAR PERMEABILITY

REFERENCE TO RELATED APPLICATION

This application claims priority from U.S. Provisional Patent Application Ser. No. 60/832,362, filed Jul. 21, 2006, the entire content of which is incorporated herein by reference.

GOVERNMENT SPONSORSHIP

The subject matter of this application was researched by the National Institute of Health under Contract No. EY016413. Accordingly, the United States government may have certain rights in this invention.

FIELD OF THE INVENTION

The present invention relates generally to compositions and methods for regulating one or more isoforms of protein kinase C. In particular embodiments, the present invention relates to compositions and methods for treating conditions associated with excessive permeability of tight junctions between cells by inhibition of protein kinase C zeta.

BACKGROUND OF THE INVENTION

Tight junctions, or zonula occludens, are structures which allow for strict regulation of passage of material between cells. Dysregulation at tight junctions has severe consequences for the cell and tissue environment and is present in a number of diseases and disorders such as diabetic macular edema.

A number of proteins have been characterized as present in tight junctions, including for instance occludin, claudin, JAM, ZO-1, 2 and 3, MAGI-1, 2, and 3, PAR3/6 and MUPP1. Regulation of these proteins, their levels, localization, and structural characteristics, may play a role in normal functioning as well as in disease states of an organism. Post-translation modification, such as phosphorylation, is a mechanism of protein regulation.

Vascular Endothelial Growth Factor (VEGF) has been shown to stimulate phosphorylation of at least one tight junctions protein, occludin, with consequent induction of vascular permeability. The action of VEGF is mediated, in part, by protein kinase C (PKC) beta.

PKC designates a class of kinases which play central roles in key cell signaling processes such as gene expression and regulation of cell growth. There are numerous isoforms of PKC and these are typically classified as: 1) "calcium-dependent" conventional isoforms which are regulated by both calcium and diacylglycerol, such as PKC-beta; 2) "calcium-independent" novel isoforms which are regulated by diacylglycerol but do not require calcium, such as PKC-delta; and 3) "atypical" isoforms which do not require calcium for activation and which are not regulated by diacylglycerol. PKC zeta is an "atypical" PKC isoform.

In this context, it is of interest that protein kinase C beta inhibitors are currently undergoing phase 3 clinical trials for the treatment of macular edema in diabetic retinopathy. However, it is found that inhibition of PKC beta prevents only about 50% of VEGF induced endothelial permeability in primary retinal endothelial cell culture.

Thus, there is a continuing need for compositions including a PKC inhibitor which regulates tight junction permeability and methods for regulating tight junction permeability in healthy and diseased cells and tissues.

Furthermore, protein kinase C isoforms are present in a variety of cell types and have been associated with a number of pathological diseases and disorders. There is a continuing need for compositions and methods of regulating PKC activity in vitro and in vivo.

SUMMARY OF THE INVENTION

A method of inhibiting PKC zeta is provided by embodiments of the present invention which includes incubating a PKC zeta inhibitor of the present invention with PKC zeta.

A method of treating or preventing a disease or disorder in a subject is provided by the present invention which includes administering a composition including a therapeutically effective amount of a protein kinase C (PKC) zeta inhibitor to the subject. A disease or disorder treated or prevented by administration of a PKC zeta inhibitor is characterized by abnormal vascular permeability.

In particular embodiments, the PKC zeta inhibitor is an inhibitor of phosphorylation of a tight junction protein, such as occludin or other proteins that control cell to cell interactions which regulate vascular permeability.

Diseases or disorders treated or prevented by administration of a composition including a therapeutically effective amount of a PKC zeta inhibitor include a microvascular complication of a systemic condition in the subject, such as diabetes.

In further embodiments, a disease or disorder treated or prevented by administration of a composition including a therapeutically effective amount of a PKC zeta inhibitor is a neoplastic disease or disorder. An antineoplastic therapeutic agent is optionally included in a composition of the present invention and/or administered to a subject in need thereof separately from the PKC zeta inhibitor.

In further embodiments, a disease or disorder treated or prevented by administration of a composition including a therapeutically effective amount of a PKC zeta inhibitor is an ischemic condition in which blood flow is severely reduced or blocked, typically due to stenosis or occlusion of a blood vessel. For example, stroke is an ischemic condition characterized by abnormal vascular permeability. Specifically, abnormal vascular permeability in stroke patients is often observed during release of vessel obstruction and subsequent reperfusion which is associated with increased blood vessel permeability.

VEGF induced abnormal vascular permeability is inhibited by administration of a PKC zeta inhibitor according to particular embodiments of the present invention.

An administered protein kinase C zeta inhibitor is a peptide protein kinase C zeta inhibitor, a non-peptide protein kinase C zeta inhibitor; or a combination thereof.

In particular embodiments, a method of the present invention includes administration of a therapeutically effective amount of the protein kinase C zeta inhibitor of formula (A), described herein, or a pharmaceutically acceptable salt, hydrate or prodrug thereof.

In further particular embodiments, a method of the present invention includes administration of a therapeutically effective amount of the protein kinase C zeta inhibitor of formula (I), described herein, or a pharmaceutically acceptable salt, hydrate or prodrug thereof.

In further particular embodiments, a method of the present invention includes administration of a therapeutically effective amount of the protein kinase C zeta inhibitor of formula (II), described herein, or a pharmaceutically acceptable salt, hydrate or prodrug thereof.

In further particular embodiments, a method of the present invention includes administration of a therapeutically effective amount of the protein kinase C zeta inhibitor of formula (III), described herein, or a pharmaceutically acceptable salt, hydrate or prodrug thereof.

In further particular embodiments, a method of the present invention includes administration of a therapeutically effective amount of the protein kinase C zeta inhibitor of formula (IV), described herein, or a pharmaceutically acceptable salt, hydrate or prodrug thereof.

In further particular embodiments, a method of the present invention includes administration of a therapeutically effective amount of the protein kinase C zeta inhibitor of formula (V), described herein, or a pharmaceutically acceptable salt, hydrate or prodrug, thereof.

Two or more protein kinase C zeta inhibitors are administered in embodiments of a method of treating or preventing a disease or disorder of the present invention. The two or more protein kinase C zeta inhibitors are administered together in a single composition, or separately. For example, two or more protein kinase C zeta inhibitors having structural formula (A) described herein are administered in admixture in a composition or separately in embodiments of a method of treating or preventing a disease or disorder of the present invention.

Also provided are embodiments in which two or more protein kinase C zeta inhibitors having structural formula (I), (II), (III), (IV) or (V) described herein are administered in admixture in a composition or separately in embodiments of a method of treating or preventing a disease or disorder of the present invention.

A therapeutically effective amount of a protein kinase C beta inhibitor is administered in embodiments of a method of treating or preventing a disease or disorder of the present invention. The protein kinase C beta inhibitor is administered together with a protein kinase C zeta inhibitor in a single composition, or the protein kinase C beta inhibitor and the protein kinase C zeta inhibitor are administered separately.

Further provided are compositions according to the present invention formulated for administration to a subject for the treatment or prevention of abnormal vascular permeability which include a protein kinase C zeta inhibitor and a pharmaceutically acceptable carrier.

A protein kinase C zeta inhibitor included in a composition of the present invention is a peptide protein kinase C zeta inhibitor, a non-peptide protein kinase C zeta inhibitor; or a combination thereof.

In particular embodiments, a composition of the present invention includes a therapeutically effective amount of the protein kinase C zeta inhibitor of formula (I), (II), (III), (IV) and/or (V) described herein, or a pharmaceutically acceptable salt, hydrate or prodrug thereof. In further particular embodiments, a composition of the present invention includes a therapeutically effective amount of the protein kinase C zeta inhibitor of formula

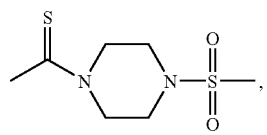
(A)

where $R_1$ and $R_2$ are each independently an alkoxycarbonyl group, a substituted alkoxycarbonyl group, an aryl group or a substituted aryl group, where at least one of $R_1$ and $R_2$ is an alkoxycarbonyl group or a substituted alkoxycarbonyl group and at least one of $R_1$ and $R_2$ is an aryl group or a substituted aryl group; where $R_3$ and $R_4$ are each independently H, a $C_1$-$C_3$ alkyl group, a substituted $C_1$-$C_3$ alkyl group or NHR5 where $R_5$ is H,

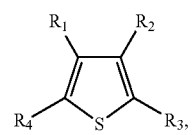

acyl or substituted acyl, where at least one of $R_3$ and $R_4$ is NHR$_5$ or a pharmaceutically acceptable salt, hydrate or prodrug thereof.

A PKC zeta inhibitor included in a composition in particular embodiments of the present invention is the PKC zeta pseudosubstrate myr-SIYRRGARRWRKL (SEQ ID No. 1).

Two or more protein kinase C zeta inhibitors are included in an inventive composition in embodiments of the present invention.

For example, two or more protein kinase C zeta inhibitors having structural formula

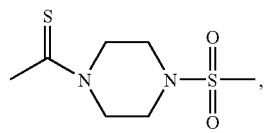
(A)

where $R_1$ and $R_2$ are each independently an alkoxycarbonyl group, a substituted alkoxycarbonyl group, an aryl group or a substituted aryl group, where at least one of $R_1$ and $R_2$ is an alkoxycarbonyl group or a substituted alkoxycarbonyl group and at least one of $R_1$ and $R_2$ is an aryl group or a substituted aryl group; where $R_3$ and $R_4$ are each independently H, a $C_1$-$C_3$ alkyl group, a substituted $C_1$-$C_3$ alkyl group or NHR5 where $R_5$ is H,

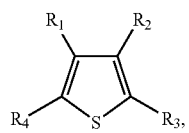

acyl or substituted acyl, where at least one of $R_3$ and $R_4$ is NHR$_5$, or a pharmaceutically acceptable salt, hydrate or prodrug thereof, are included in a composition according to embodiments of the present invention.

Also provided are embodiments in which two or more protein kinase C zeta inhibitors having structural formula (I), (II), (III), (IV) or (V) described herein are included in an inventive composition in embodiments of the present invention.

In further embodiments, a therapeutically effective amount of a protein kinase C beta inhibitor is admixed with a protein kinase C zeta inhibitor in a composition.

Optionally, an antineoplastic therapeutic agent is included in a composition according to embodiments of the present invention.

A method of inhibiting PKC zeta is provided which includes incubating PKC zeta with a PKC zeta inhibitor having the structural formula:

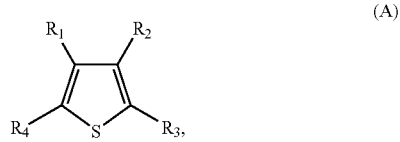
(A)

where $R_1$ and $R_2$ are each independently an alkoxycarbonyl group, a substituted alkoxycarbonyl group, an aryl group or a substituted aryl group, where at least one of $R_1$ and $R_2$ is an alkoxycarbonyl group or a substituted alkoxycarbonyl group and at least one of $R_1$ and $R_2$ is an aryl group or a substituted aryl group; where $R_3$ and $R_4$ are each independently H, a $C_1$-$C_3$ alkyl group, a substituted $C_1$-$C_3$ alkyl group or NHR5 where $R_5$ is H,

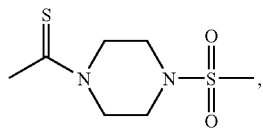

acyl or substituted acyl, where at least one of $R_3$ and $R_4$ is $NHR_5$.

A method of inhibiting PKC zeta includes inhibiting PKC zeta in vitro where the PKC zeta is present in an intact cell in particular embodiments of the present invention. A method of inhibiting PKC zeta includes inhibiting isolated PKC zeta in vitro. In particular embodiments, the PKC zeta is in a sample isolated from a subject.

PKC zeta inhibited according to a method of the present invention is human and/or non-human PKC zeta.

DETAILED DESCRIPTION OF THE INVENTION

Figure 1:
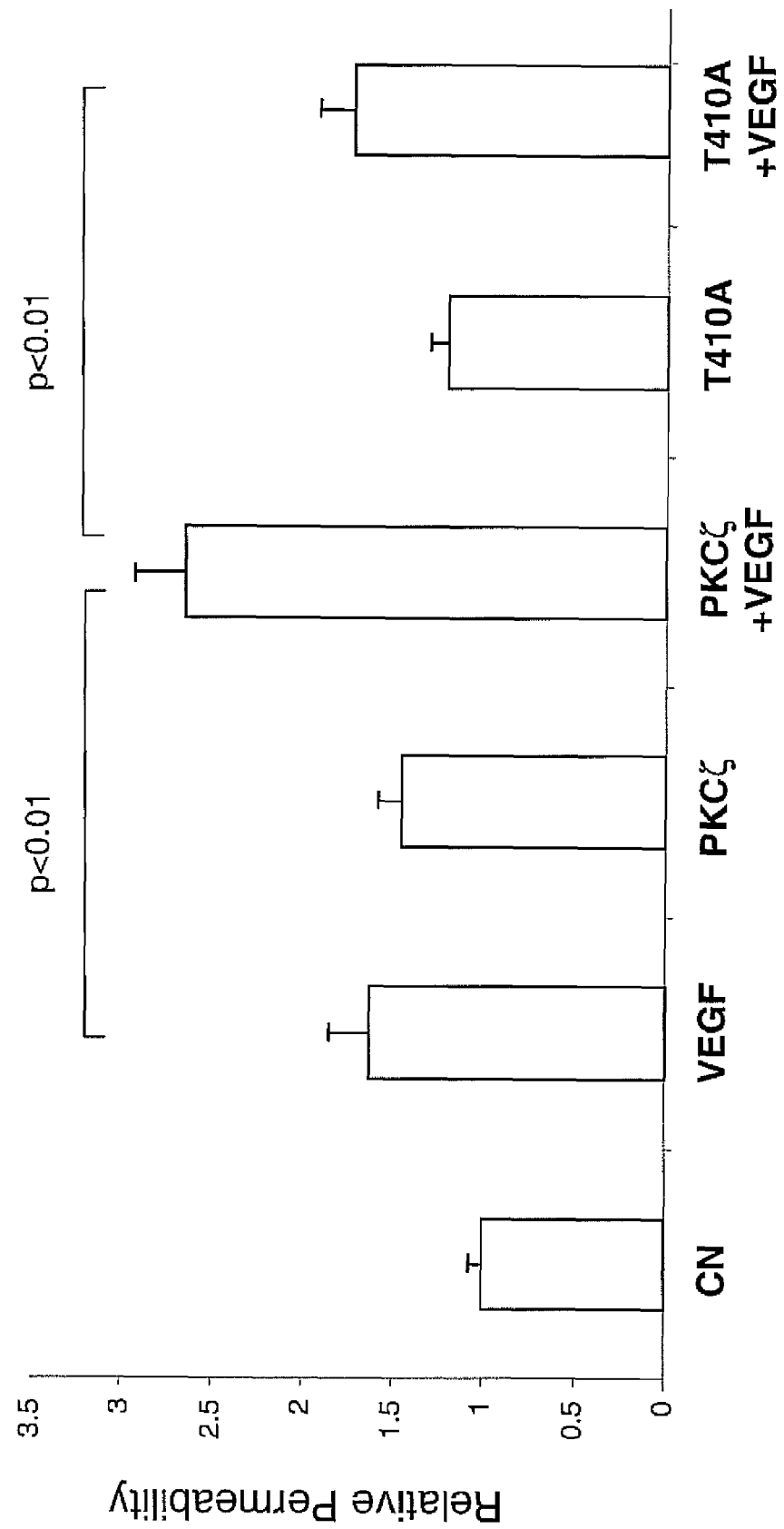
FIG. 1 is a graph showing that transfection of exogenous PKC zeta into bovine retinal endothelial cells (BREC) augments the VEGF induction of permeability to 70kDa dextran over vector transfected control cells whereas transfection of inactive PKC zeta which has threonine 410 mutated to alanine, T410A, does not augment VEGF induced permeability.

Compositions according to the present invention include one or more protein kinase C zeta inhibitors. Such compositions have utility in preventing or reducing phosphorylation of a PKC zeta substrate. For example, compositions including a PKC zeta inhibitor are useful in treating disease states characterized by undesirable PKC zeta activity.

PKC zeta is known in the art and is identified in various species, for instance, by antibodies which react specifically with PKC zeta protein. PKC zeta has been cloned and the nucleic acid and amino acid sequences are known, including for example, human PKZ zeta described in Kochs, G. et al., Eur. J. Biochem., 216(2):597-606, 1993.

The term "PKC zeta inhibitor" refers to a synthetic or naturally occurring molecule that inhibits an activity of a PKC zeta enzyme. A PKC zeta inhibitor inhibits an activity of a PKC zeta enzyme where a statistically significant difference in a PKC zeta activity is detected in an assay performed in the presence of the inhibitor compared to the same assay performed in the absence of the inhibitor. For example, a PKC zeta inhibitor inhibits phosphorylation of a synthetic or natural substrate for a PKC zeta enzyme where a statistically significant reduction of phosphorylation of a synthetic or natural substrate for PKC zeta is detected in the presence of the inhibitor and no statistically significant reduction of phosphorylation of the substrate is detected in the absence of the inhibitor.

A peptide PKC zeta inhibitor is included in a composition of the present invention in specific embodiments. For example, the myristoylated PKC zeta pseudosubstrate myr-SIYRRGARRWRKL (SEQ ID No. 1), also termed PKCζI for PKC zeta Inhibitor herein, is characterized as an inhibitor of PKC zeta activity. The art recognized conventional amino acid abbreviations are used to represent the above-mentioned peptide.

A peptide inhibitor of PKC zeta is synthesized according to methods known in the art, illustratively including chemical synthesis and recombinant molecular biological techniques as described in Atherton, E., Sheppard, R. C., Solid Phase peptide synthesis: a practical approach. Oxford University Press, Oxford, England, 1989; Sambrook et al., Molecular Cloning: A Laboratory Manual, Cold Spring Harbor Laboratory Press, 2001; and Ausubel, F. et al., Eds., Short Protocols in Molecular Biology, Wiley, 2002.

A non-peptide PKC zeta inhibitor is included in a composition of the present invention in further embodiments. In preferred embodiments a non-peptide inhibitor is an organic molecule having a molecular weight in the range of about 200-2000 g/mol and having the structural formula

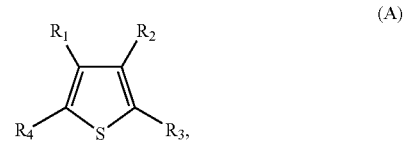
(A)

where $R_1$ and $R_2$ are each independently an alkoxycarbonyl group, a substituted alkoxycarbonyl group, an aryl group or a substituted aryl group, where at least one of $R_1$ and $R_2$ is an alkoxycarbonyl group or a substituted alkoxycarbonyl group and at least one of $R_1$ and $R_2$ is an aryl group or a substituted aryl group; where $R_3$ and $R_4$ are each independently H, a $C_1$-$C_3$ alkyl group, a substituted $C_1$-$C_3$ alkyl group or $NHR_5$ where $R_5$ is H,

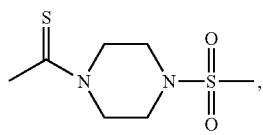

acyl or substituted acyl, where at least one of $R_3$ and $R_4$ is $NHR_5$.

In particular embodiments, a PKC zeta inhibitor has the structural formula

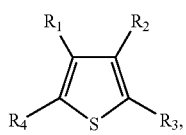

(A)

where $R_1$ and $R_2$ are each independently a tert-butoxycarbonyl group or ethoxycarbonyl group, a phenyl group, a dichlorophenyl group or methoxybenzene, where at least one of $R_1$ and $R_2$ is a tert-butoxycarbonyl group or ethoxycarbonyl group and at least one of $R_1$ and $R_2$ is a phenyl group, a dichlorophenyl group or methoxybenzene; where $R_3$ and $R_4$ are each independently H, methyl, or $NHR_5$ where $R_5$ is H,

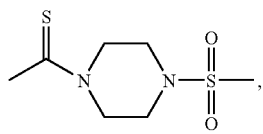

or acetyl, where at least one of $R_3$ and $R_4$ is $NHR_5$.

The term "alkoxycarbonyl" refers to the group $C(O)OR_6$, where $R_6$ is $C_1$-$C_4$ straight chain or branched alkyl or substituted straight chain or branched alkyl. Examples of alkoxycarbonyl groups include methoxycarbonyl, ethoxycarbonyl, tert-butoxycarbonyl, isobutoxycarbonyl, n-butoxycarbonyl, propoxycarbonyl and isopropoxycarbonyl.

The term "aryl" refers to monocyclic or bicyclic aromatic hydrocarbon rings having from 6-12 carbon atoms in the ring or rings. The monocyclic or bicyclic aromatic hydrocarbon rings may be heterocyclic, having one or more heteroatoms, such as S, O, N or P atoms, in the ring or rings. Examples of aryl groups include phenyl, napthalenyl, piperazinyl, biphenyl and diphenyl.

The term "substituted aryl" refers to an aryl group having a substituent at any substitutable position.

The term "substituted alkoxycarbonyl" refers to an alkoxycarbonyl group having a substituent at any substitutable position.

The term "substituted $C_1$-$C_3$ alkyl" refers to a $C_1$-$C_3$ alkyl group having a substituent at any substitutable position.

The term "substituted acyl" refers to an acyl group having a substituent at any substitutable position.

Examples of substituents include alkyl, substituted alkyl, hydroxy, alkylthio, alkylsulfonyl, alkylsulfinyl, alkoxy, alkoxyalkyl, alkoxycarbonyl, alkoxyarylthio, alkoxycarbonyl, alkylcarbonyloxy, aryl, aryloxy, arylalkyl, arylalkyloxy, arylsulfinyl, arylsulfinylalkyl, arylsulfonylaminocarbonyl, alkanoyl, substituted alkanoyl, alkanoylamino, alkylcarbonyl, aminocarbonylaryl, aminocarbonylalkyl, arylazo, alkoxycarbonylalkoxy, arylcarbonyl, alkylaminocarbonyl, aminoalkylcarbonyl, arylaminocarbonyl, alkylcarbonyloxy, alkylcarbonyloxy, alkylcarbonylamino, arylcarbonylamino, arylsulfonyl, alkenyl, substituted alkenyl, alkynyl, substituted alkynyl, amino, substituted amino, aminoalkyl, substituted aminoalkyl, alkylamino, substituted alkylamino, disubstituted amino, aminocarbonyl, arylamino, arylalkylamino, arylalkoxy, arylsulfonylamino, arylalkenyl, aryloxycarbonyl, arylthio, arylthioalkyl, arylalkylthio, cyano, cycloalkyl, substituted cycloalkyl, cycloalkylalkyl, cycloalkylalkoxy, carboxyl, substituted carboxyl, carboxyalkyl, carboxyalkoxy, carbamoyl, halogen, haloalkyl, haloalkoxy, heterocycloalkyl, substituted heterocycloalkyl, heterocycloalkylalkyl, heteroaryl, substituted heteroaryl, heteroarylthio, heteroaryloxy, heteroarylalkenyl, heteroarylheteroaryl, heteroarylalkylthio, heteroaryloxyalkyl, heteroarylsulfonyl, heterocycloalkylsulfonyl, nitro, sulfonic acid, sulfonamide, substituted sulfonamide, thio, thioalkyl, and ureido.

In particular embodiments, a compound characterized as having an inhibitory effect on the activity of PKC zeta has the structural formula (I):

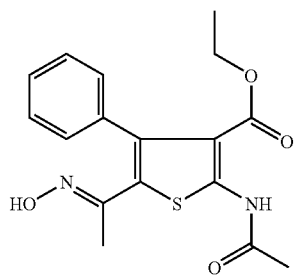

(I)

The compound of formula (I), ethyl (5E)-2-acetylimino-5-[1-(hydroxyamino)ethylidene]-4-phenyl-thiophene-3-carboxylate, also called PKC-zeta I1, PKCzI-1 and PKCζI-1 herein, has a half-maximal inhibitory concentration, $IC_{50}$, of 10 micromolar for PKC-zeta. In contrast, the compound of formula (I) has an $IC_{50}$ of greater than 100 micromolar for PKC-delta and for PKC-beta.

In further particular embodiments, a compound characterized as having an inhibitory effect on the activity of PKC zeta has the structural formula (II):

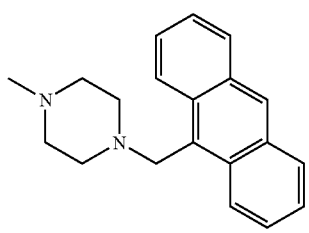

(II)

The compound of formula (II), 1-(anthracen-9-ylmethyl)-4-methyl-piperazine, has an $IC_{50}$ of 25 micromolar for PKC zeta and an $IC_{50}$ of 50 micromolar for PKC-beta. This compound has an $IC_{50}$ of greater than 100 micromolar for PKC-delta.

In other embodiments, a compound characterized as having an inhibitory effect on the activity of PKC zeta has the structural formula (III):

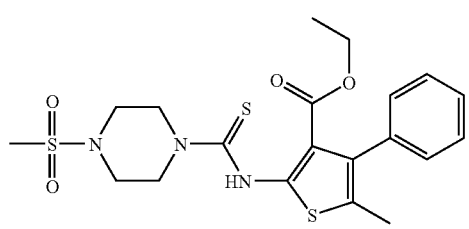
(III)

The compound of formula (III) inhibits PKC zeta with 1.2-fold greater efficacy than the compound of formula (I) when tested at 100 micromolar as described in Example 11.

In particular embodiments, a compound characterized as having an inhibitory effect on the activity of PKC zeta has the structural formula (IV):

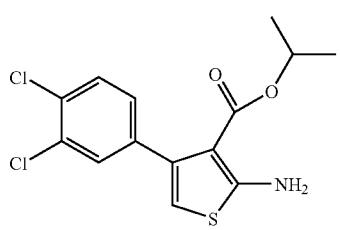
(IV)

The compound of formula (IV) inhibits PKC zeta with 1.8-fold greater efficacy than the compound of formula (I) when tested at 100 micromolar as described in Example 11.

In particular embodiments, a compound characterized as having an inhibitory effect on the activity of PKC zeta has the structural formula (V):

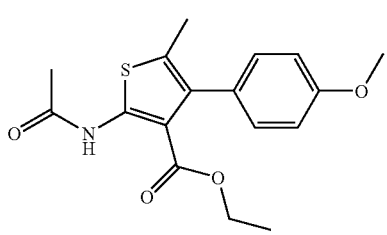
(V)

The compound of formula (V) inhibits PKC zeta with 2.6-fold greater efficacy than the compound of formula (I) when tested at 100 micromolar as described in Example 11.

The thiophene compounds described herein, such as compounds of formulas (A), (I), (II), (III), (IV) and (V), may be synthesized according to standard organic synthetic methods as described herein and known to those of skill in the art For example, a Gewald reaction, shown in Scheme 1 and described in detail in Gewald, K., et al., 1966, Heterocycles from CH-acidic nitriles, VIII, 2-Aminothiophenes from methylene-active nitrites, carbonyl compounds, and sulfur, Chemische Berichte, 99:94-100; and Sabnis, R. W., et al., 1999, 2-Aminothiophenes by the Gewald reaction, Journal of Heterocyclic Chemistry, 36:333-345, may be used to synthesize a tetrasubstituted thiophene (4).

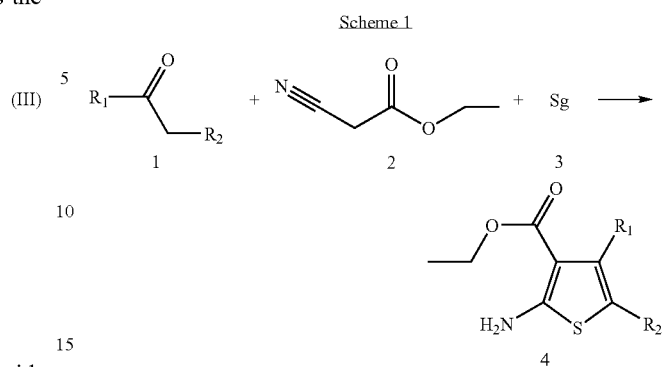

In Scheme 1, $R_1$ is an aryl group or substituted aryl group and $R_2$ is H, a $C_1$-$C_3$ alkyl group, or a substituted $C_1$-$C_3$ alkyl group. The starting material (1) in Scheme 1 is commercially available or may be synthesized according to standard organic synthetic methods. In an example of this synthetic method, cyanoacetic acid ethyl ester and elemental sulfur are reacted with an alpha-methylene ketone to provide the tetrasubstituted thiophene.

A further method for synthesis of a thiophene PKC zeta inhibitor is shown in Scheme 2.

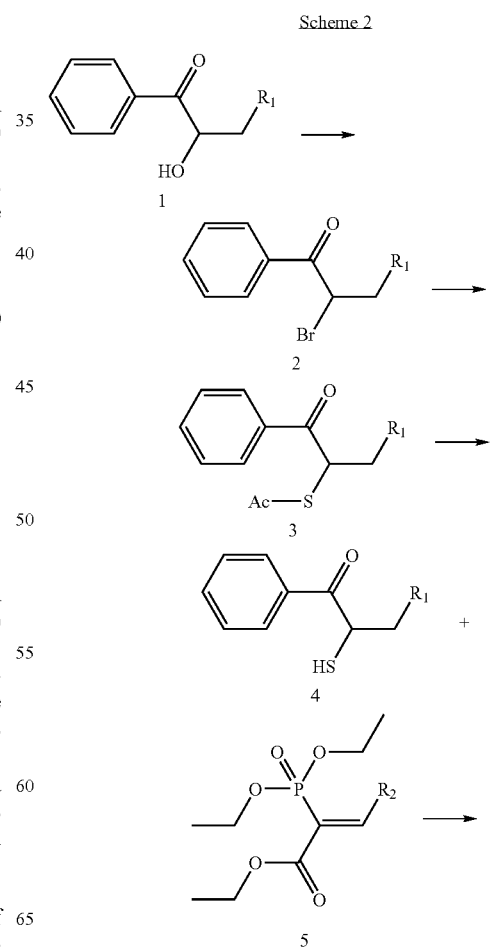

-continued

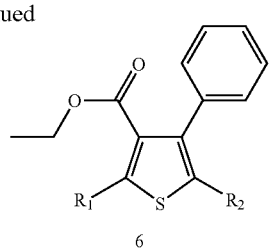

6

Scheme 2 illustrates a synthetic scheme for a thiophene compound including synthesis of an aromatic alpha-mercaptoketone from the starting material (1) using the method described in detail in Coppola, G. M., et al., 1995, Synthesis of highly functionalized thiophenes. 4-Aryl-3-carboxylate derivatives, Synlett., 11:1143-1144. The aromatic alpha-mercaptoketane is reacted with vinyl phosphonate, oxidized with DDQ and reduced with hydride to form the thiophenes shown at (6) in Scheme 2. $R_1$ is amino or substituted amino and $R_7$ is H, a $C_1$-$C_3$ alkyl group, or a substituted $C_1$-$C_3$ alkyl group.

A further method for synthesis of a thiophene compound described herein is illustrated in Scheme 3.

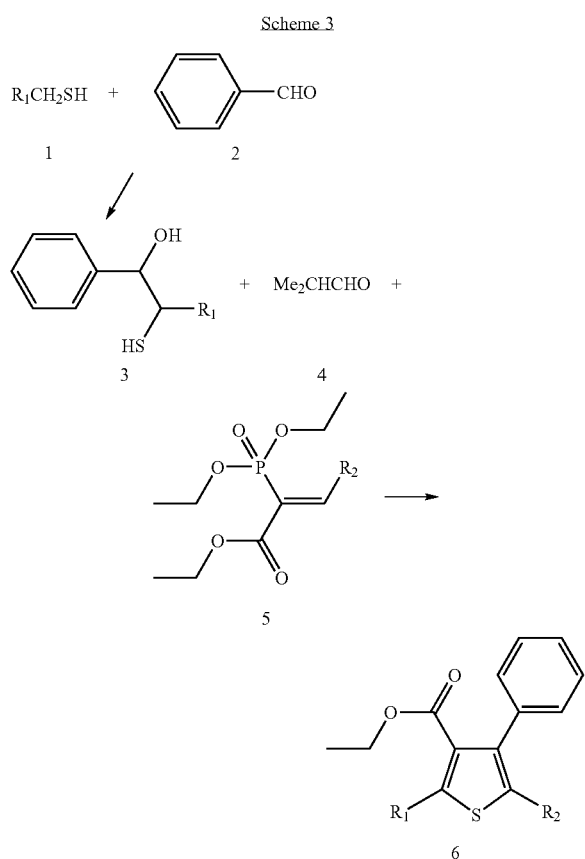

Scheme 3 illustrates a synthetic method using a methylenethiol starting material, where $R_1$ is amino or substituted amino. Further details of reaction Scheme 3 are described in Damon, R. E., II, and Wareing, J. R. 1989. Preparation and formulation of 7-(butyl- or thienyl)-3,5-dihydroxy-6-heptenoate mevalonate analogs as anticholesteremics, U.S. Pat. No. 4,829,081.

Alternatively, the compounds of formulas (I), (II), (III), (IV) and (V) may be obtained commercially. For example, the compound of formula (I) is available as compound number 5634152 from ChemBridge Corp., San Diego, Calif., USA. The compound of formula (II) is available as compound number 5421928 from ChemBridge Corp., San Diego, Calif., USA. The compound of formula (III) is available as compound number 7828306 from ChemBridge Corp., San Diego, Calif., USA. The compound of formula (IV) is available as compound number 6131246 from ChemBridge Corp., San Diego, Calif., USA. The compound of formula (V) is available as compound number 7943464 from ChemBridge Corp., San Diego, Calif., USA.

In particular embodiments, a composition is provided according to the present invention which includes a PKC zeta inhibitor and a pharmaceutically acceptable carrier.

The term "pharmaceutically acceptable carrier" as used herein refers to a carrier or diluent that is generally non-toxic to an intended recipient and which does not significantly inhibit activity of the protein kinase C zeta inhibitor or other active agent included in the composition.

A composition according to the present invention generally includes about 0.1-99% of a protein kinase C zeta inhibitor.

A protein kinase C zeta inhibitor is included in a composition of the present invention in the form of a free acid or free base in particular embodiments. In further embodiments, a protein kinase C zeta inhibitor is included in a composition in the form of a pharmaceutically acceptable salt such as an acid or base addition salt. A pharmaceutically acceptable salt refers to any salt form of a protein kinase C zeta inhibitor that is generally non-toxic to an intended recipient and which does not significantly inhibit activity of the protein kinase C zeta inhibitor or other active agent included in the composition. A protein kinase C zeta inhibitor is included in a composition in the form of a hydrate in embodiments of the present invention.

A protein kinase C zeta inhibitor prodrug is included in a composition according to particular embodiments of the present invention. A protein kinase C zeta inhibitor prodrug is a form of a protein kinase C zeta inhibitor covalently bound to a moiety which is released from the protein kinase C zeta inhibitor yielding the intact active protein kinase C zeta inhibitor. Prodrug forms are well known in the art as exemplified in Sloan, K. B., Prodrugs, M. Dekker, New York, 1992; and Testa, B. and Mayer, J. M., Hydrolysis in drug and prodrug metabolism: chemistry, biochemistry, and enzymology, Wiley-VCH, Zurich, 2003.

More than one inhibitor of PKC zeta is included in a composition according to embodiments of the present invention. Thus, for example, in particular embodiments a peptide inhibitor of PKC zeta and a non-peptide inhibitor of PKC zeta are both included in a composition. In a further example, two or more non-peptide inhibitors of PKC zeta are included in a composition according to embodiments of the present invention.

In addition, a synergistic effect of administration of a protein kinase C zeta inhibitor and an inhibitor of a second isoform of PKC is likely to be observed. Thus, in further preferred embodiments, a method according to the present invention includes administration of a protein kinase C zeta inhibitor and an inhibitor of a second isoform of PKC. PKC inhibitors suitable for administration with a protein kinase C zeta inhibitor to treat abnormal vascular permeability include an inhibitor of a "calcium-dependent" isoform, also called conventional or cPKC isoforms, such as an inhibitor of PKC alpha, PKC beta, and/or PKC gamma; an inhibitor of a "calcium-independent" isoform, also called novel or nPKC isoforms, such as an inhibitor of PKC delta, PKC epsilon and/or PKC eta; or a second "atypical" isoform, such as an inhibitor PKC iota and/or PKC lambda.

Examples of suitable inhibitors of a second isoform of PKC illustratively include bisindoylmaleimides such as bisindoylmaleimide I, an inhibitor of cPKC. Bisindoylmaleimide I is known in the art and may be obtained by standard organic synthetic methods or obtained commercially, such as from Calbiochem Corp., La Jolla, Calif.

An inhibitor of protein kinase C zeta and an inhibitor of PKC beta are included in a composition according to embodiments of the present invention.

Particular inhibitors of PKC beta include ruboxistaurin and salt forms thereof such as ruboxistaurin mesylate, also known as LY333531. Bisindoylmaleimide I and LY379196 are further examples of PKC beta inhibitors.

In further embodiments, a composition of the present invention optionally includes a PKC zeta inhibitor and a second therapeutic agent other than a PKC inhibitor.

A composition according to the present invention may be formulated in various forms. A composition formulated for oral administration may be a solid, semi-solid or liquid formulation prepared according to methods known in the art and including any of various conventional pharmaceutical ingredients.

Solid dosage forms for oral administration include capsules, tablets, pills, powders, and granules. In such solid dosage forms, a protein kinase C zeta inhibitor is admixed with at least one pharmaceutically acceptable carrier such as a filler or extender, as for example, starches, lactose, sucrose, glucose, mannitol, and silicic acid; a binder, as for example, carboxymethylcellulose, alignates, gelatin, polyvinylpyrrolidone, sucrose, and acacia; a humectant, as for example, glycerol; a disintegrating agent, as for example, agar-agar, calcium carbonate, plant starches such as potato or tapioca starch, alginic acid, certain complex silicates, and sodium carbonate; a solution retarder, as for example, paraffin; an absorption accelerator, as for example, quaternary ammonium compounds; a wetting agent, as for example, cetyl alcohol, glycerol monostearate, and glycols; an adsorbent, as for example, kaolin and bentonite; a buffering agent, such as sodium citrate and dicalcium phosphate; and a lubricant, as for example, talc, calcium stearate, magnesium stearate, solid polyethylene glycols and sodium lauryl sulfate. Mixtures of these or other pharmaceutically acceptable carriers may also be included in embodiments of a composition of the present invention.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

The enteric coating is typically a polymeric material. Preferred enteric coating materials have the characteristics of being bioerodible, gradually hydrolyzable and/or gradually water-soluble polymers. The amount of coating material applied to a solid dosage Generally dictates the time interval between ingestion and drug release. A coating is applied with a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present invention to achieve delivery of the active to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particular enteric coating material is those acrylic acid polymers and copolymers available under the trade name EUDRAGIT®, Roehm Pharma (Germany). The EUDRAGIT® series L, L-30D S copolymers, and cross-linked polymers, see for example U.S. Pat. No. 6,136,345, are suitable in particular applications since these are insoluble in the stomach and dissolve in the intestine.

The enteric coating optionally contains a plasticizer to prevent the formation of pores and cracks that allow the penetration of the gastric fluids into the solid dosage. Suitable plasticizers illustratively include, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

The enteric coating is applied to a solid dosage using conventional coating methods and equipment. For example, an enteric coating can be applied to a solid dosage using a coating pan, an airless spray technique, fluidized bed coating equipment, or the like. Detailed information concerning materials, equipment and processes for preparing coated dosage forms may be found in Pharmaceutical Dosage Forms: Tablets, eds. Lieberman et al. (New York: Marcel Dekker, Inc., 1989), and in L. V. Allen, Jr. et al., Ansel's Pharmaceutical Dosage Forms and Drug Delivery Systems, 8th Ed. (Philadelphia, Pa.: Lippincott, Williams & Wilkins, 2004).

Liquid dosage forms for oral administration include a pharmaceutically acceptable carrier formulated as an emulsion, solution, suspension, syrup, or elixir in particular embodiments. In addition to the protein kinase C zeta inhibitor, the liquid dosage forms may contain one or more pharmaceutically acceptable carriers commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and/or other such conventional pharmaceutical ingredients.

A composition formulated for oral administration can also include adjuvants, such as wetting agents, emulsifying and suspending agents, sweetening, flavoring, and perfuming agents.

Suspensions, in addition to a protein kinase C zeta inhibitor, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and/or other such conventional pharmaceutical ingredients.

In particular embodiments, a composition including a PKC zeta inhibitor of the present invention is formulated as a physiologically acceptable sterile aqueous or nonaqueous solution, dispersion, suspension, emulsion, or sterile powder for reconstitution into a sterile injectable solution or dispersion. Examples of suitable aqueous and nonaqueous carriers, include diluents, solvents, and vehicles such as water, ethanol, polyols such as propylene glycol, polyethylene glycol, glycerol, and the like, and suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate.

Such formulations are administered by a suitable route including parenteral and oral administration. Administration may include systemic or local injection, such as intravenous injection.

A composition of the present invention may also contain one or more adjuvants such as preserving, wetting, emulsifying, and dispensing agents. Prevention of the action of microorganisms can be ensured by various antibacterial and antifungal agents, for example, parabens, chlorobutanol, phenol and sorbic acid. It may also be desirable to include an isotonic agent, exemplified by sugars and sodium chloride. Prolonged delivery of an injectable pharmaceutical form can be achieved by the use of agents delaying absorption, for example, aluminum monostearate and gelatin.

Detailed information concerning materials, equipment and processes for preparing and manufacturing various dosage forms may be found in Pharmaceutical Dosage Forms: Tablets, eds. H. A. Lieberman et al., New York: Marcel Dekker, Inc., 1989, and in L. V. Allen, Jr. et al., Ansel's Pharmaceutical Dosage Forms and Drug Delivery Systems, 8th Ed., Philadelphia, Pa.: Lippincott, Williams & Wilkins, 2004. Further examples and details of pharmacological formulations and ingredients are found in standard references such as: A. R. Gennaro, Remington: The Science and Practice of Pharmacy, Lippincott Williams & Wilkins, 20th ed., 2003; L. V. Allen, Jr. et al., Ansel's Pharmaceutical Dosage Forms and Drug Delivery Systems, 8th Ed., Philadelphia, Pa., Lippincott, Williams & Wilkins, 2004; and J. G. Hardman et al., Goodman & Gilman's The Pharmacological Basis of Therapeutics, McGraw-Hill Professional, 10th ed., 2001.

A composition including a PKC zeta inhibitor may be administered by a systemic route and/or by a local route. Suitable routes of administration illustratively include intravenous, oral, buccal, parenteral, intrathecal, intracerebroventricular, intraperitoneal, ocular, intraocular, rectal, vaginal, subcutaneous, intradermal, intramuscular, topical, intranasal, otic and mucosal. A composition of the present invention maybe administered by intratumoral and/or peritumoral routes where applicable.

In particular embodiments of a method of preventing or treating a disease or disorder characterized by abnormal vascular permeability, a composition including a PKC zeta inhibitor is administered locally at or near a site of abnormal vascular permeability. In a specific example, a composition including a PKC zeta inhibitor is administered locally to one or both eyes of a subject having or at risk of having macular edema associated with diabetic retinopathy. Ocular administration includes intraocular periocular routes of administration. Ocular administration further includes administration by injection or other methods under the surface membrane of the eye to diffuse through the sclera into the retina, vitreous and anterior chamber of the eye. In particular embodiments, a composition including a PKC zeta inhibitor is administered intravitreally, to the subconjunctiva and/or via a sub-Tenon's capsule route.

A method of preventing or treating a disease or disorder characterized by abnormal vascular permeability is provided according to the present invention which includes administering a therapeutically effective amount of a composition including a PKC zeta inhibitor to a subject in need thereof. In particular embodiments a composition according to the present invention is administered to a subject having a disease or disorder or at risk for a disease or disorder characterized by abnormal vascular permeability.

The term "therapeutically effective amount" as used herein is intended to mean an amount of an inventive composition which is effective to alleviate, ameliorate or prevent a symptom or sign of a condition to be treated. In particular embodiments, a therapeutically effective amount is an amount which has a beneficial effect in a subject having macular edema associated with diabetic retinopathy, brain edema associated with a brain tumor or stroke, an abnormal cell proliferation disorder such as cancer, a tumor, a benign growth or other condition responsive to a protein kinase C zeta inhibitor of the present invention.

Thus, for example, in particular embodiments, treatment of a subject to prevent or treat a disease or disorder characterized by abnormal vascular permeability is characterized by prevention or amelioration of the abnormal vascular permeability. Abnormal vascular permeability, and change in abnormal vascular permeability is assessed by techniques known in the art and described herein.

The term "subject" refers to any individual to whom a composition of the present invention is administered. The term "subject" includes mammals and birds, particularly humans, non-human primates, cats, dogs, cows, horses, rodents, pigs, sheep, gand poultry.

A disease or disorder to be prevented or treated using methods and compositions according to the present invention is a disease or disorder characterized by abnormal vascular permeability.

The terms "abnormal permeability of tight junctions" and "abnormal vascular permeability" as used herein are intended to indicate a physiological state characterized by passage of material across a physiological barrier which would ordinarily be prevented or reduced in a healthy individual. Abnormal permeability may be assessed, for example, by administration of a substance known to be prevented from passing across a physiological barrier including tight junctions and assay for the presence of the substance in a location from which it is generally excluded. Exemplary permeability assays for assessment of tight junctions, vessel permeability, and the effects of PKC zeta inhibitors in vitro and in vivo are described herein.

Tight junctions are involved in various physiological barriers illustratively including barriers such as the blood-brain barrier, blood-nerve barrier, and blood-retina barrier. Tight junctions are found in various tissues, including blood vessels, intestine, lung and kidney, for example.

In particular embodiments, compositions according to the present invention which include an inhibitor of PKC zeta are provided which are administered to treat vascular disorders. For example, microvascular complications are typically seen in diabetic neuropathy, diabetic nephropathy and diabetic retinopathy. Further examples of diseases or disorders prevented or treated according to the present invention include eye conditions such as diabetic retinopathy, age-related macular degeneration and retinopathy of prematurity.

In further embodiments, a disease or disorder treated or prevented by administration of a composition including a therapeutically effective amount of a PKC zeta inhibitor is an ischemic condition in which blood flow is severely reduced or blocked, typically due to stenosis or occlusion of a blood vessel. For example, stroke is an ischemic condition characterized by abnormal vascular permeability. Specifically, abnormal vascular permeability in stroke patients is often observed during release of vessel obstruction and subsequent reperfusion which is associated with increased blood vessel permeability.

A composition of the present invention is administered for beneficial effect in the treatment of various diseases and disorders characterized by abnormal cell growth, including neoplastic diseases and disorders in particular embodiments. Neoplastic diseases and disorders have been observed to be associated with abnormal permeability of tight junctions, for example as described in Soler A. P. et al., Carcinogenesis, 20(8);1425-31, 1999.

Neoplastic diseases and disorders illustratively include adenocarcinomas, arrhenoblastomas, astrocytomas, basal cell carcinomas, bladder carcinomas, breast carcinomas, cervical carcinomas, choriocarcinoma, colorectal carcinomas, endometrial carcinoma, endometrial hyperplasia, esophageal carcinomas, fibrosarcomas, gastric carcinomas, glioblastomas, carcinomas of the head and neck, hemangiomas, hemangioblastomas, hepatoblastomas, Kaposi's sarcoma, kidney carcinomas, laryngeal carcinomas, leiomyosarcomas, leukemias, liver carcinomas, lung carcinomas, lymphomas, medulloblastomas, melanomas, nasopharyngeal carcinomas, neuroblastomas, oligodendrogliomas, osteogenic sarcomas, ovarian carcinomas, pancreas carcinomas, prostate carcinomas, renal cell carcinoma, retinoblastomas, rhabdomyosarcomas, Schwannomas, squamous cell carcinomas, thecomas, thyroid carcinomas urinary tract carcinomas and uterine carcinomas.

The amount of a composition of the present invention administered to a subject and the route of administration depends on factors such as the identity of the particular protein kinase C zeta inhibitor included in the composition, the identity and the severity of the condition or disease affecting the subject, the rate of uptake and excretion of the inhibitor, and the general physical characteristics of the subject including age, gender and body weight. One of skill in the art could determine a therapeutically effective amount and route of administration in view of these and other considerations typical in medical practice.

In general, a therapeutically effective amount of a protein kinase C zeta inhibitor in a composition is in the range of about 0.001 mg/kg-100 mg/kg body weight. In particular embodiments, a therapeutically effective amount of a protein kinase C zeta inhibitor in a composition is in the range of about 0.01-10 mg/kg, and in further embodiments, a therapeutically effective amount of a protein kinase C zeta inhibitor in a composition is in the range of about 0.1-5 mg/kg. A therapeutically effective amount of a composition of the present invention may be manufactured and/or administered in single or multiple unit dose forms.

In some embodiments, a method according to the present invention includes administering a therapeutic agent in addition to administering a PKC zeta inhibitor. A therapeutic agent may be any of various agents suitable for use in conjunction with a particular disease or disorder. For example, a therapeutic agent is an antineoplastic therapeutic agent in one embodiment of the present invention.

Antineoplastic therapeutic agents illustratively include alkylating agents, antibiotics, folate inhibitors, purine analogs, pyrimidine analogs, and radiosensitizing compounds. Specific antineoplastic therapeutic agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, droloxifene, dromostanolone, duazomycin, edatrexate, eflomithine, elsamitrucin, enloplatin, enpromate, epipropidine, epirubicin, erbulozole, esorubicin, estramustine, estramustine, etanidazole, etoposide, etoposide, etoprine, fadrozole, fazarabine, fenretinide, floxuridine, fludarabine, fluorouracil, flurocitabine, fosquidone, fostriecin, fulvestrant, gemcitabine, gemcitabine, hydroxyurea, idarubicin, ifosfamide, ilmofosine, interleukin II (IL-2, including recombinant interleukin II or rIL2), interferon alpha-2a, interferon alpha-2b, interferon al[ha-n1, interferon alpha-n3, interferon beta-Ia, interferon gamma-I b, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, methotrexate, metoprine, meturedepa, mitindomide, mitocarcin, mitocromin, mitogillin, mitomalcin, mitomycin, nitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, puromycin, pyrazofurin, riboprine, rogletimide, safingol, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, triethylenemelamine, trimetrexate, triptorelin, tubulozole, uracil mustard, uredepa, vapreotide, verteporlin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin. A therapeutic agent may also be a pharmaceutically acceptable salt, ester, amide, hydrate, and/or prodrug of any of these or other therapeutic agents. These and other antineoplastic therapeutic agents are described, for example, in Goodman & Gilman's The Pharmacological Basis of Therapeutics, McGraw-Hill Professional, 10th ed., 2001.

An aspect of microvascular complications of various diseases, such as diabetes, characterized by abnormal vascular permeability is induction of increased permeability of endothelial cell tight junctions by VEGF. Surprisingly, PKC zeta inhibition is found to be more effective than PKC beta inhibitors at preventing VEGF induced permeability as determined by the present invention.

Without wishing to be bound by theoretical considerations, a mechanism of VEGF activity in increasing permeability of endothelial cell tight junctions is found to be phosphorylation of one or more tight junction proteins. Thus, in a specific embodiment, an included PKC zeta inhibitor is an inhibitor of VEGF stimulation of occludin phosphorylation.

A method of inhibiting PKC zeta is provided according to embodiments of the present invention which includes incubating PKC zeta with a PKC zeta inhibitor having the structural formula:

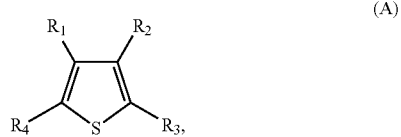
(A)

where $R_1$ and $R_2$ are each independently an alkoxycarbonyl group, a substituted alkoxycarbonyl group, an aryl group or a substituted aryl group, where at least one of $R_1$ and $R_2$ is an alkoxycarbonyl group or a substituted alkoxycarbonyl group and at least one of $R_1$ and $R_2$ is an aryl group or a substituted aryl group; where $R_3$ and $R_4$ are each independently H, a $C_1$-$C_3$ alkyl group, a substituted $C_1$-$C_3$ alkyl group or $NHR_5$ where $R_5$ is H,

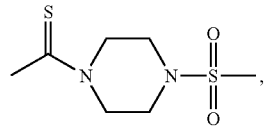

acyl or substituted acyl, where at least one of $R_3$ and $R_4$ is $NHR_5$, a salt, hydrate or prodrug thereof.

In particular embodiments, a method of inhibiting PKC zeta includes incubating PKC zeta with a PKC zeta inhibitor having the structural formula (I), (II), (III), (IV) and/or (V), a salt, hydrate or prodrug thereof.

Amounts of a PKC zeta inhibitor used in a method to inhibit PKC zeta and times of incubation depend on the application and will be determined by one of skill in the art without undue experimentation. For example, the $IC_{50}$ value for a particular PKC zeta inhibitor is determined.

Methods of inhibiting PKC zeta provided by the present invention have utility, for instance, in assays directed to elucidation of signal transduction pathways in cells in vitro and in vivo.

Broadly described, a method of inhibiting PKC zeta according to embodiments of the present invention includes incubating PKC zeta, such as PKC zeta in a cell or tissue, in vitro or in vivo, PKC zeta in an organism, and/or PKC zeta in an isolated sample, with a PKC zeta inhibitor.

Incubation of a cell or tissue, in vitro or in vivo, an organism, and/or an isolated sample with a PKC zeta inhibitor is optionally followed by assay of the effects of inhibition of PKC zeta in the cell, tissue, organism or sample.

Thus, for example, to determine whether PKC zeta mediates growth factor effects on cell growth in particular cells, the cells are incubated with or without a PKC zeta inhibitor and cell growth in response to application of a growth factor is measured by a standard cell growth indicator such as quantitation of incorporation of tritiated thymidine into DNA. PKC zeta is determined to mediate effects of the growth factor on cell growth where a specific effect of the PKC zeta inhibitor is detected.

Assays for PKC zeta activity may be performed on any material suspected of containing PKC zeta, such as a sample from a subject, cultured primary cells and/or tissues or cells lines. Assays for PKC zeta activity may be performed using synthetic PKC zeta, such as PKC zeta generated recombinantly in a cell in vivo or in vitro. Thus, for example, PKC zeta activity is assessed by incubation of a sample suspected of containing PKC zeta with a PKC zeta substrate, and detection of phosphorylation of the substrate, such as by detection of incorporation of radiolabeled phosphorus in the substrate. Incubation of the sample with a PKC zeta inhibitor described herein allows for detection of specific PKC zeta activity.

A sample from a subject may be a sample of a tissue, such as a biopsy sample, cells, a bodily fluid which may or may not include cells illustratively including blood, plasma, serum, saliva, mucous, semen, tears, an ocular exudate, a tumor exudate, ascites fluid, lymph and urine.

In further embodiments, an inhibitor of PKC zeta activity is used in a method of inhibiting PKC zeta which is more effective to inhibit PKC zeta than to inhibit PKC beta or PKC delta. For example, the compound of formula (I) has a half-maximal inhibitory concentration, $IC_{50}$, of 10 micromolar for PKC-zeta, an $IC_{50}$ of greater than 100 micromolar for PKC-delta and for PKC-beta indicating that the compound of formula (I) is more effective to inhibit PKC zeta than to inhibit PKC beta or PKC delta. In a further example, the compound of formula (II) has an $IC_{50}$, of 25 micromolar for PKC zeta, an $IC_{50}$ of 50 micromolar for PKC-beta and an $IC_{50}$ of greater than 100 micromolar for PKC-delta, indicating that the compound of formula (II) is more effective to inhibit PKC zeta than to inhibit PKC beta or PKC delta.

A method of inhibiting PKC zeta is applicable to inhibition of human PKC zeta as well as non-human PKC zeta. In particular embodiments, a method of inhibiting PKC zeta includes incubation of a PKC zeta inhibitor having the structural formula:

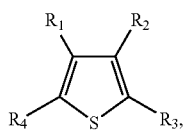

(A)

where $R_1$ and $R_2$ are each independently an alkoxycarbonyl group, a substituted alkoxycarbonyl group, an aryl group or a substituted aryl group, where at least one of $R_1$ and $R_2$ is an alkoxycarbonyl group or a substituted alkoxycarbonyl group and at least one of $R_1$ and $R_2$ is an aryl group or a substituted aryl group; where $R_3$ and $R_4$ are each independently H, a $C_1$-$C_3$ alkyl group, a substituted $C_1$-$C_3$ alkyl group or $NHR_5$ where $R_5$ is H,

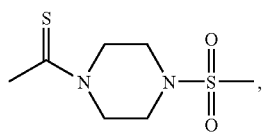

acyl or substituted acyl, where at least one of $R_3$ and $R_4$ is $NHR_5$, a salt, hydrate or prodrug thereof and/or a PKC zeta inhibitor having the structural formula (I), (II), (III), (IV) and/or (V), a salt, hydrate or prodrug thereof, with non-human PKC zeta, such as PKC zeta of non-human primates, cats, dogs, cows, horses, rodents, pigs, sheep, goats and poultry or other non-human mammal or bird.

Embodiments of inventive compositions and methods are illustrated in the following examples. These examples are provided for illustrative purposes and are not considered limitations on the scope of inventive compositions and methods.

EXAMPLES

Example 1

In vitro Models for Characterization of Permeability of Tight Junctions

Isolation of Retinal Capillary Endothelial Cells

Retinal capillaries are isolated from bovine eyes obtained from a local slaughterhouse. The capillary preparation is passed through a series of meshes and collagenase treatment to remove associated cells. Media with D-Valine is used when first plating the cells since endothelial cells have the isomerase to convert the D amino acid to its L isoform while contaminating pericytes do not and are, therefore, selected out. All steps are conducted under sterile conditions with gloves.

Ten to twenty bovine whole eyes from recently slaughtered animals are transported on ice from a local abattoir. The cell isolation procedure usually occurs up to 24 his post-mortem. Optimal cell yields are obtained from retinas extracted from eyeballs of cows slaughtered within the last 24 hours. Keeping the eyeballs on ice and bathed in an antiseptic solution is imperative to achieve a viable, high-yielding, uncontaminated primary cell preparation.

The whole eyes are bathed in a 10% povidone-iodine solution for a minimum of 5 minutes. With a sterile scalpel, a circumferential cut 5 mm posterior to the limbus is made to open the eyeball for retina removal. After the vitreous and lens are extracted, the retina is gently separated and cut from the anterior portion of the eyeball using sterile tweezers. The retinas are rinsed three times in ice-cold MEM D-Valine with HEPES buffer and pooled in the same solution. In a laminar flow hood, the retinas are washed with the same solution through a 185-micron nylon mesh stretched over a sterile porcelain funnel placed on a vacuum flask to remove retinal pigment epithelial cells. The retinal tissue is removed from the mesh and brought to a volume of 30 mL with ice-cold MEM D-Val with HEPES. Next, the retinal aliquot is homogenized on ice six times in a Teflon/glass Potter-Elvehjem type tissue grinder with 0.25 mm clearance at 250 rpm. The homogenate is centrifuged at 400×g for 10 minutes at 4° C. After resuspending the pelleted retinal tissue in 10 mL of 4° C. $Ca^{++}$, $Mg^{++}$ free PBS, the suspension is shaken or inverted 3 to 4 times and kept on ice. The isolated microvessel fragments are trapped on an 88 micron nylon mesh over a funnel as above. The nylon mesh is then cut from the funnel and placed in a glass petri dish. The microvessels are separated from the mesh by repeated rinses with $Ca^{++}$, $Mg^{++}$ free PBS and transferred to a 50 mL conical tube. The microvessels are then pelleted at 400×g at 4° C. for 10 minutes. The pelleted microvessels are resuspended in 10 mL of enzyme cocktail and incubated at 37° C. on a rocker for 45 to 60 minutes to separate the pericytes. Note that the enzyme cocktail can be stored frozen in aliquots (−20° C.) but only for a maximum time of 6 months. Continual rocking at 37° C. during the enzyme digestion step is necessary for complete separation of the pericytes. The digestion is halted when observation with a Nikon phase contrast microscope shows release of the pericytes. The vessel preparation is passed over a 53 micron nylon mesh without suction; the mesh is transferred to a 50 mL conical tube, and the vessel fragments are separated from the mesh by washing with ice-cold Modified Eagle's Medium with D-Valine. This suspension is centrifuged at 400×g for 5 minutes at 4° C., resuspended in 10 mL of MEM D-Val, and centrifuged again. The resulting pellet is resuspended in 5 mL of the standard growth medium consisting of MEM D-Val supplemented with 20% fetal calf serum, 50 micrograms/mL ECUS, 16 U/nL heparin, 0.01 mL/mL MEM vitamins, 0.01 mL/mL glutamine, and 0.02 mL/mL antibiotic/antimycotic. The vessel fragments are plated on a 25 cm² tissue culture flask precoated with fibronectin at 2 micrograms/cm² and are grown in a humidified incubator at 37° C. with 95% $CO_2$, 5% $O_2$. Using a 0.1% solution of fibronectin from bovine plasma to coat the tissue culture surface is recommended for successful adherence of the endothelial cells. The medium is removed and fresh medium is added 24 hours following the plating.

Culture of Retinal Capillary Endothelial Cells

Colonies of endothelial cells grow from the isolated microvessels after 5-7 days. They are removed with 0.05% trypsin and reseeded onto a 75 cm² tissue culture flask precoated with 1 microgram/cm² fibronectin. Endothelial cells do not reach confluence with the primary seeding and should be split and re-seeded when islands of endothelial cells arise, prior to the proliferation of pericytes. The cells are repeatedly subcultured with 0.05% trrpsin when approximately 80% confluent and expanded for experimental use at a ratio of 1:3. Subculturing the cells at 80% confluence at a ratio of 1:3 will ensure continued proliferation and homology of the cell population. Be careful not to over-trypsinize the cells when subculturing, usually 2 min of treatment with trypsin is sufficient time to release the majority of cells.

At passage 3 the cells in 10% DMSO are routinely frozen in liquid nitrogen for storage purposes.

The bovine retinal endothelial cells (BREC) are used experimentally at 6 to 10 passages after primary culture.

Retinal cells are cultured in supplemented MCDB-131 media. A more robust and consistent cell growth occurs using this medium rather than the MEM D-Val media used in cell isolation. The cell culture should appear homogeneous with a cobblestone-like appearance. Contaminating pericytes are much larger than endothelial cells and can cause areas of endothelial cell death making useful transport studies impossible.

To verify that the culture contains only endothelial cells the preparations are grown on glass coverslips and immunostained for the endothelial specific marker Von Willebrand factor.

Transendothelial Electrical Resistance Measurements

Transendothelial electrical resistance (TER) is a measurement of ion flux across the endothelial monolayer. This is a rapid and simple measure of barrier integrity. Alterations to TER most likely reflect changes in the junctional complex.

Briefly, the endothelial cells are grown to confluence on a porous transwell filter coated with 1 microgram/cm$^2$ fibronectin.

To measure resistance, the transwell filters are placed in an Endohm™ chamber, which contains two concentric voltage sensing electrodes, one at the top and one at the bottom. The Endohm™ is connected to an EVOM™ resistance meter. Ion flux is determined by applying a pulse of known amplitude across the endothelial monolayer and measuring the corresponding transendothelial voltage deflection. Ohm's law is then used to calculate resistance across the cross sectional area which is expressed in ohms ($\Omega \times cm^2$). The investigator should be sure to subtract the resistance of a blank, fibronectin coated, transwell filter from each sample tested.

Solute Flux Measurement

Solute flux across endothelial monolayers is determined by placing labeled sugars or proteins on the apical side of the monolayer and determining accumulation in the basolateral chamber over time. The choice of solute may reflect very different features of the endothelial barrier, dextran, for example, is often used since there are no known cell receptors for dextran that may contribute a specific transport mechanism. Also, one should be aware of the size, shape (globular or linear) and hydrophobicity of the chosen solutes. A number of solutes have been used for flux rate determinations including smaller dextrans, as well as mannitol and inulin. The use of albumin is of physiologic relevance as it crosses the blood-retinal barrier in various retinal pathologies and it is useful to compare its rate of transport to that of dextran of a similar molecular weight since albumin may have a transcellular and paracellular transport component. In addition, since the relationship between fluorescence intensity and solute concentration is linear, a standard curve to determine the concentration of solute that crossed the barrier can be generated.

Endothelial cells are grown to confluence on transwell filters. After the cells have grown to confluence, an additional 2 to 4 days is necessary to allow formation of a tight barrier. This may vary depending on the cell preparation.

Solute flux is measured by applying 10 micromolar or 20 micromolar RITC-dextran or FITC-BSA to the apical chamber of inserts with a confluent endothelial cell monolayer. The specific experiment may dictate when to perturb the system with, for example, a PKC inhibitor, relative to the time of measuring flux. Remember to consider the time for the perturbation to effect transport rates, for example, time for synthesis and assembly or disassembly of the junctional complex.

One half-hour after addition of fluorescent solute, 50 microliter samples are taken from the basolateral chamber. This is continued on the half-hour for up to four hours. The samples are placed into the 96 well black/clear bottom plate. A sample is taken from the apical chamber at the last time point and also placed in the 96 well plate. In pilot studies, it is critical to demonstrate that the amount of fluorescence in the apical chamber remains essentially unchanged over the course of the experiment. Fluorescence of each aliquot is quantified on a fluorescence plate reader. We use a FluorImager 595. A blank sample with media only but no fluorescent marker should be used for background subtraction. The rate of diffusive flux ($P_o$) is calculated by the following formula at each time point: $P_o=[(F_A/\Delta t)V_A]/(F_L A)$ where $P_o$=diffusive flux (cm/s); $F_A$=basolateral fluorescence; $F_L$=apical fluorescence; $\Delta t$=change in time; A=surface area of the filter (cm$^2$); $V_A$=volume of the basolateral chamber (cm$^3$). Note that unless the volume removed from the basolateral chamber is replaced, the volume in the basolateral chamber changes for each time point calculated. The data may be reduced as a rate over the total time course of the experiment if the change remains linear. This is done by plotting the change in fluorescence accumulated in the basolateral chamber corrected for fluorescence in the apical chamber, volume and area versus time and then determining the slope of the straight line or rate of diffusive flux, $P_o$.

The fluorescence obtained from each time point is normalized to the fluorescence in the apical chamber. Next this ratio is corrected for the volume in the bottom chamber and this corrected ratio is plotted verses time to determine the rate of fluorescent molecule accumulation by obtaining the slope. Finally, this slope is converted from minutes to seconds and divided by the area of the filter yielding the diffusive flux in cm/s.

Real Time Flux Measurement

A system for measurement of real time flux is described in detail in Antonetti, D. A. et al., 2002, Journal of Neurochemistry, 80:667-677. Briefly described, the system uses a plexiglass chamber into which the transwell filter is placed. Fiber optics conduct excitation laser light to the basolateral chamber and a second fiber optic conducts fluorescence emission light to a detector. In this manner real time alteration in solute flux can be determined. Furthermore, the basolateral chamber is hydraulically coupled to an external reservoir, which can be lowered in order to apply a pressure gradient across the endothelial monolayer, recapitulating in vivo conditions. Thus, the effective solute flux or $P_e$, including both diffusive and convective components can be determined. Application of the hydrostatic pressure gradient allows investigation of endothelial cell function under conditions that mimic normal physiology.

Methods described in this example are used to determine the half-maximal inhibitory concentration, $IC_{50}$, of a particular PKC zeta inhibitor. A PKC zeta inhibitor is incubated with various concentration of PKC zeta in vitro by addition of the inhibitor to cultured BREC cells, followed by the addition of a labeled permeability marker, 70 kDa RITC dextran. Results indicate that the compound of formula (I) has a half-maximal inhibitory concentration, $IC_{50}$, of 10 micromolar for PKC-zeta, an $IC_{50}$ of greater than 100 micromolar for PKC-delta and for PKC-beta indicating that the compound of formula (I) is more effective to inhibit PKC zeta than to inhibit PKC beta or PKC delta. In a further example, the compound of formula (II) has an $IC_{50}$, of 25 micromolar for PKC zeta, an $IC_{50}$ of 50 micromolar for PKC-beta and an $IC_{50}$ of greater than 100 micromolar for PKC-delta, indicating that the compound of formula (II) is more effective to inhibit PKC zeta than to inhibit PKC beta or PKC delta.

Example 2

In vivo Model for Characterization of Permeability of Tight Junctions

Vascular permeability is quantified in this in vivo model by measuring albumin leakage form blood vessels into the retina. Evans blue is an acid dye of the diazo group that noncovalently binds to albumin in the blood, allowing the breakdown in blood-retinal barrier to be detected when increased vessel leakage is extravasated into the interstitial space.

Rats are used in this example and each animal is weighed and the body weight (BW) recorded for anaesthetic and dye injections. Each animal is anesthetized by intramuscular injection of 1 microliter/g BW a Ketamine/Xylazine mixture equal to 66.7 Ketamine/6.67 mg Xylazine/kg BW.

Evans blue is injected through the femoral vein over 10 seconds at a concentration of 1 microliter/g BW, equal to 45 mg/kg BW. The dye is allowed to circulate in the animal for 2 hours. One milliliter of blood is drawn from the vena cava of the animal with a heparinized 1 milliliter syringe. The blood is transferred to a microcentrifuge tube and mixed by gently inverting the tube several times before putting the sample on ice. The blood is centrifuged at 14000 rpm for 20 minutes and the plasma is transferred to a new microcentrifuge tube and stored at −70° C.

The chest cavity of the animal is then opened and the heart is cannulated with a blunt end 18 gauge needle into the left ventricle and up into the left atrium. The right atrium is cut to release the pressure and the animal is then perfused with citrate-buffered 1% paraformaldehyde, warmed to 37° C., for 2 minutes at 66 ml/min to clear Evans blue from the vessel lumina.

Both eyes are enucleated and bisected at the equator to harvest the retinas which are optionally dried thoroughly in a Speed-Vac for 5 hours. The weight of the retinas is measured with an analytical balance. Each retina is then incubated in 200 microliters of formamide at 70° C. for 18 hours to extract the Evans blue. The retina extract is centrifuged at 70000 rpm for 45 minutes at 4° Cm the supernatant is collected and transferred to a new microcentrifuge tube.

Stock Evans blue having a concentration of 45 mg/ml is diluted with formamide for a standard curve. For example, standards having concentrations of 0.125, 0.25, 0.5, 1.0, 2.0 and 4.0 mg/ml are produced.

The obtained plasma samples are diluted 1:10000 with formamide. Fifty microliters of the standards, plasma and retina extracts are pipetted in triplicate into a 96-well plate. The absorbance in each well is measured at 620 and 740 nm with a plate reader. The background-subtracted absorbance (A620-A740) is calculated for each sample and the dye concentration is determined using the standard curve. Evans blue accumulation in the retinal parenchyma, a measure of vessel permeability of the retinal blood vessels is determined according to the following formula where P is permeability, REB is the amount of Evans blue in the retina, RW is retina weight, PEB is the concentration of Evans blue in the plasma and C is the circulation time:

$$P(\text{microliters/g/h}) = \frac{REB\,(\text{micrograms})/RW\,(g)}{PEB\,(\text{micrograms/microliter}) \times C(h)}$$

Example 3

Transfection of endothelial cells with wild-type PKC zeta confirms that this specific atypical PKC isoform contributes to VEGF induced endothelial permeability. BREC are transfected with empty vector, control condition, or wild-type human PKC zeta plasmid by electroporation using the Amaxa transfection system. The wild-type human PKC zeta plasmid is described in detail in A Romanelli, K A Martin, A Toker, and J Blenis. Molecular and Cellular Biology, 1999, v 19, p 2921-2928. Recombinant human VEGF165 is purchased from R&D Systems (Minneapolis, Minn.) for transfection. Using a green fluorescent protein as a marker, a transfection efficiency greater than 70% is possible in BREC with this system. FIG. 1 shows a graphic representation of the results of this procedure and illustrates that transfection of PKC zeta (PKCζ) into BREC augments the VEGF induction of permeability to 70 kDa dextran over vector transfected control cells whereas transfection of inactive PKC zeta which has threonine 410 mutated to alanine, T410A, does not augment VEGF induced permeability. These data support a role for PKC zeta in regulation of VEGF induced permeability. Statistical analysis by Anova followed by Tukey's post-test with an n of 4 for all samples except T410A and T410A+VEGF where n=3.

Example 4

Figure 2:
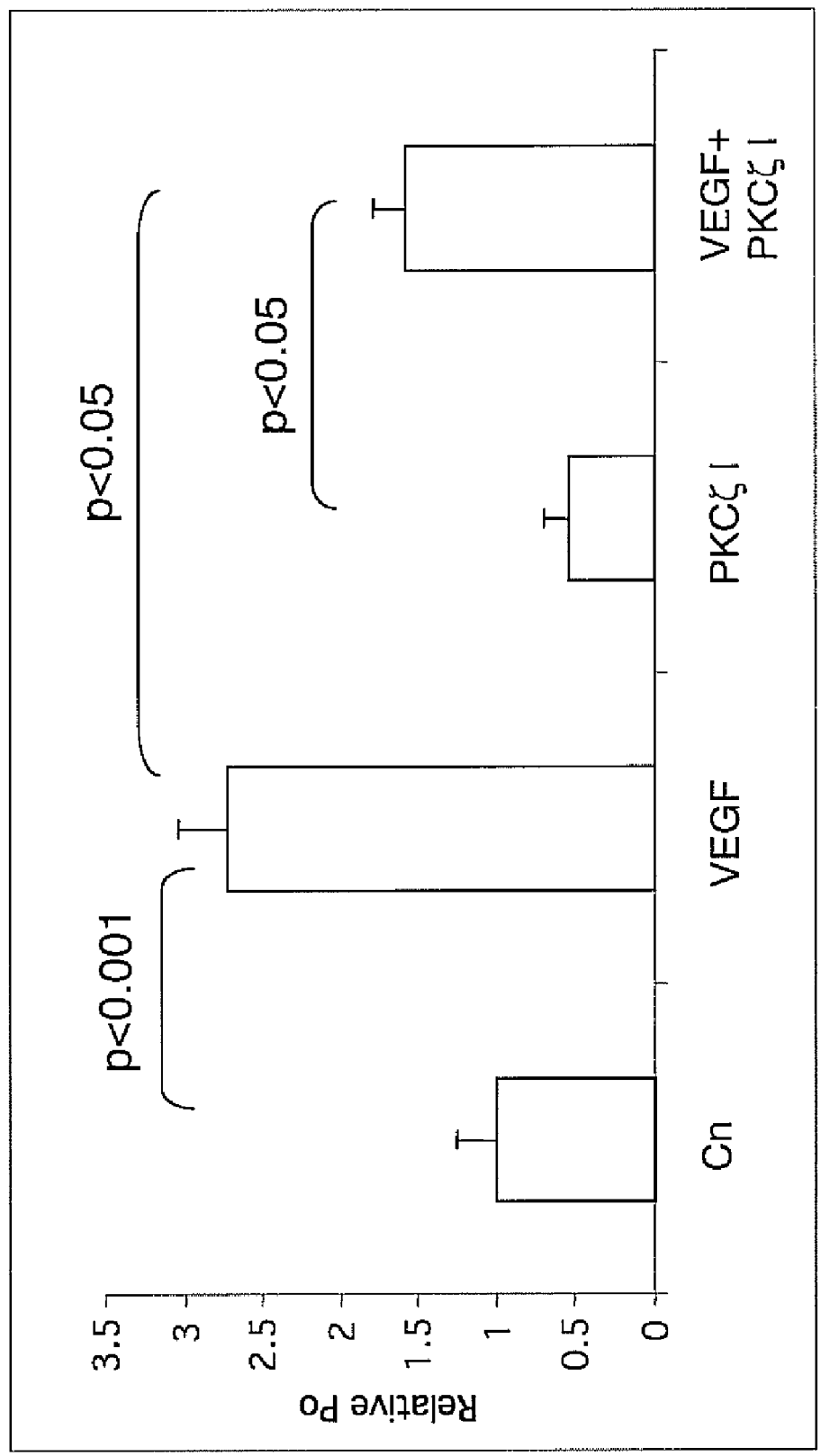
FIG. 2 is a graph showing that inhibition of PKC zeta activity with the peptide inhibitor myr-SIYRRGARRWRKL reduces and prevents a VEGF stimulated increase in permeability.

The use of the myristoylated peptide inhibitor of PKC zeta (PKCζ I) of SEQ ID No. 1 demonstrates that PKC zeta contributes to VEGF stimulated endothelial permeability. Bovine retinal endothelial cells (BREC) are grown to confluence on transwell filters (Costar) and treated with hydrocortisone (100 nM) to induce barrier properties. PKC zeta peptide inhibitor (50 nM, Calbiochem) is applied to the cells 30 min before addition of fluorescent-labeled tracer and VEGF (50 ng/mL, R&D Systems) is applied to the cells for 15 min before addition of tracer. RITC-labeled 70 kDa dextran (Sigma) is used as a tracer for cell permeability measures and is applied to the apical chamber at 10 micromolar. Samples are drawn from the basolateral chamber over a 4 h time course and the rate of tracer accumulation is used to determine monolayer permeability, Po, in cm/s. FIG. 2 illustrates the results of the use the myristoylated peptide inhibitor of PKC zeta on endothelial permeability to 70 kDa RITC-dextran. VEGF stimulated dextran permeability as expected in the endothelial monolayer and inhibition of PKC zeta reduced or prevented permeability. Statistical analysis of these results is by ANOVA with Tukey's post-test where n ranged from 7-10 for each group.

Example 5

Figure 3:
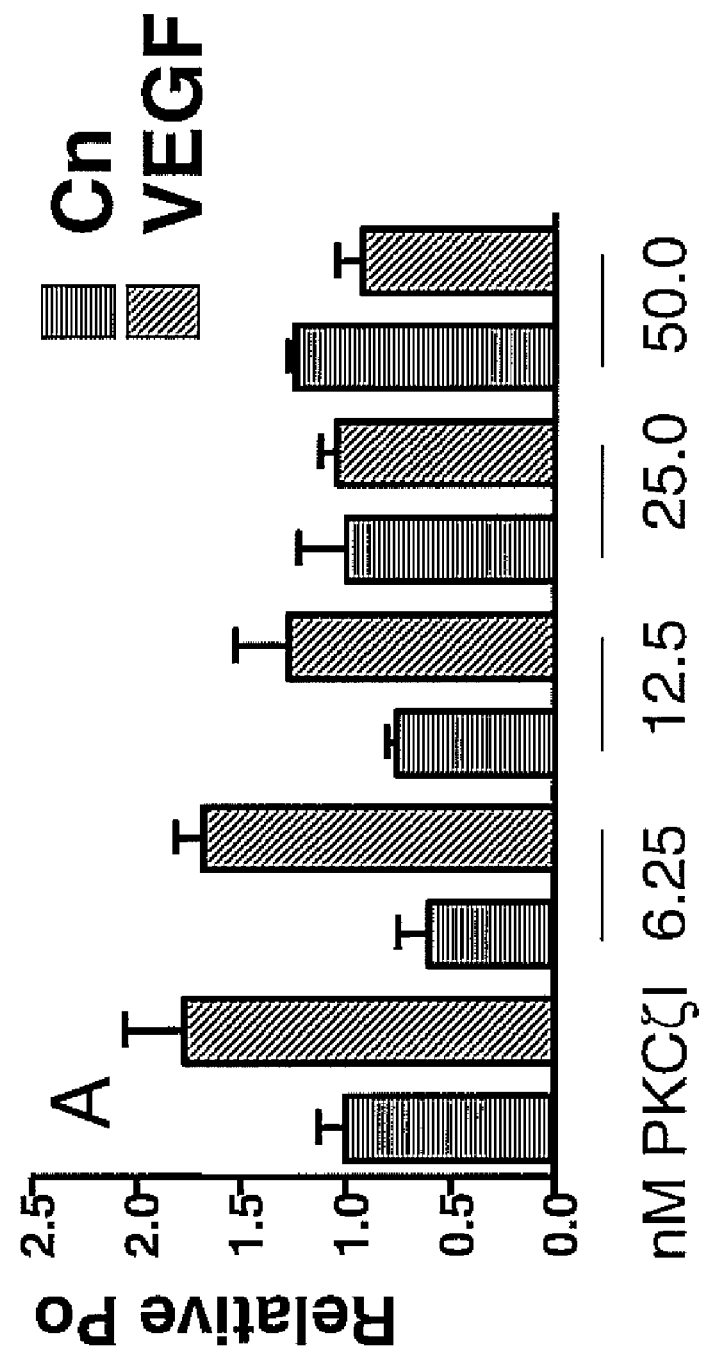
FIG. 3 is a graph showing that inhibition of PKC zeta activity with the peptide inhibitor myr-SIYRRGARRWRKL reduces VEGF stimulated endothelial permeability in a dose dependent manner.

FIG. 3 further demonstrates that inhibition of PKC zeta activity reduces VEGF stimulated endothelial permeability in a dose dependent manner. Bovine retinal endothelial cells (BREC) are grown to confluence on transwell filters (Costar) and treated with hydrocortisone (100 nM) to induce barrier properties. PKC zeta peptide inhibitor (PKCζ I) of SEQ ID No. 1 (Calbiochem) is applied to the cells at concentrations of 6.25 nM, 12.5 nM, 25 nM, and 50 nM, 30 min before addition of fluorescent-labeled tracer and VEGF (50 ng/mL, R&D Systems) is applied to the cells for 15 min before addition of tracer.

Example 6

Figure 4:
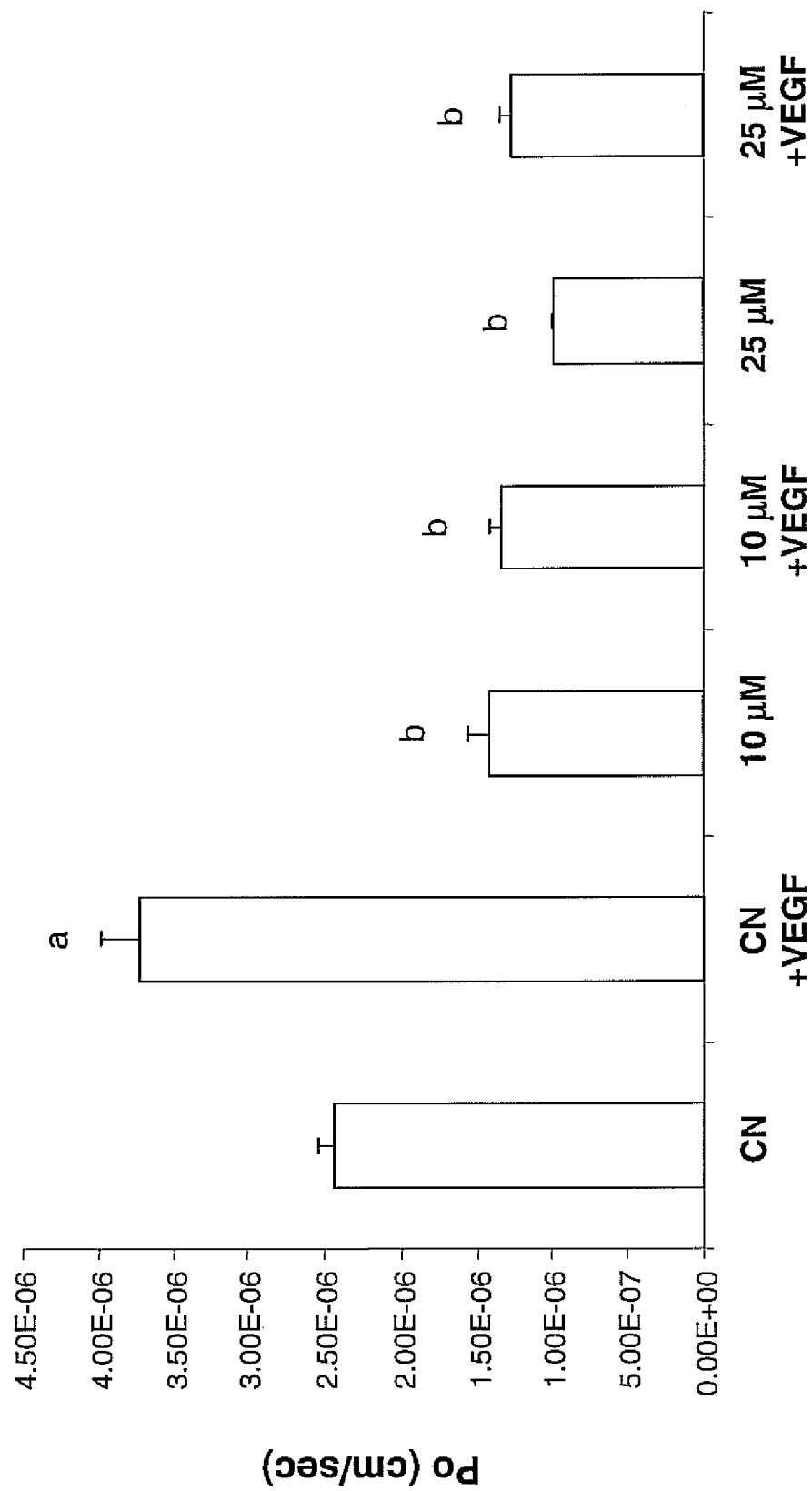
FIG. 4 is a graph showing that PKC-zeta I1 effectively blocks VEGF induced permeability in vitro.

FIG. 4 shows that PKC-zeta I1 effectively blocks VEGF induced permeability in vitro. PKC-zeta I1 at concentrations of 10 micromolar and 25 micromolar is applied to the cells 30 min before addition of fluorescent-labeled tracer and VEGF (50 ng/mL) is applied to the cells for 15 min before addition of tracer. Permeability is measured as described above. FIG. 4 demonstrates that the use of PKC-zeta I1 completely blocks VEGF induced endothelial permeability and reduces baseline permeability as well. ANOVA analysis followed by Bonferroni post-test, letter "a" indicates p<0.001 versus control, letter "b" indicates p<0.001 versus both control and VEGF.

Example 7

Figure 5:
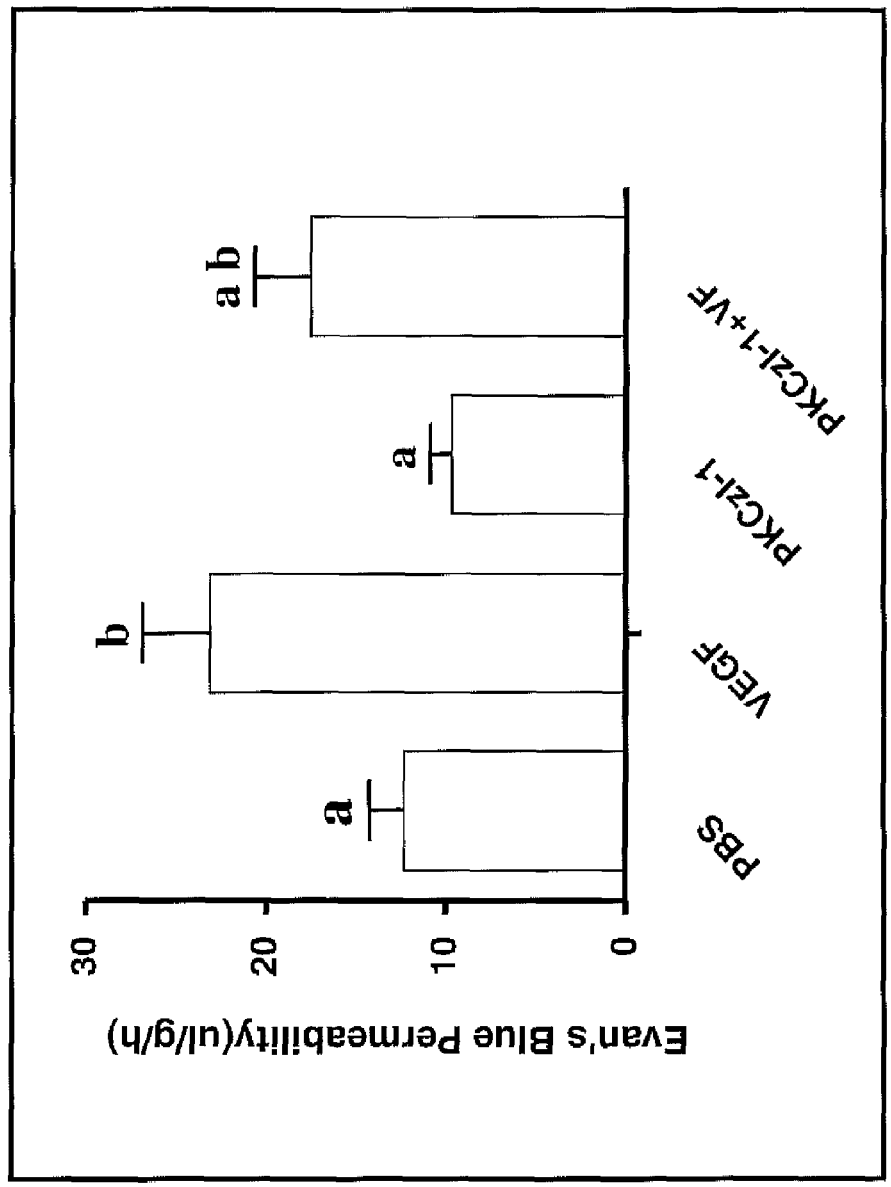
FIG. 5 is a graph showing that PKC-zeta I1 blocks VEGF induced permeability in vivo.

FIG. 5 shows that PKC-zeta I1 blocks VEGF induced permeability in vivo. The PKC-zeta I1 is effective at reducing retinal albumin flux in vivo after VEGF treatment. VEGF (50 ng) or VEGF plus PKC-zeta I1 are injected into the eyes of anesthetized rats for 5 h before harvesting retinas. The final concentration of PKC-zeta I1 in the eye is about 10 micromolar assuming a 30 microliter vitreous volume. Phosphate buffered saline (PBS) or PBS and PKC-zeta I1 are injected as well in separate eyes. Flux to albumin is measured using the albumin binding dye Evan's blue. Evan's blue is injected into the animals through the femoral vein over 10 seconds at 45 mg/kg body weight and allowed to circulate for the final 2 h before harvesting retinas. Evan's blue in the vasculature is flushed by cardiac perfusion and retinas are harvested. Evan's blue is eluted from the retinas in formamide and read spectrophotometrically. VEGF increased flux of Evan's blue bound albumin to a similar degree as is observed in vitro for 70 kDa RITC Dex permeability. The PKC-zeta I1 reduced Evan's blue bound albumin flux by 50%. Statistical analysis is by ANOVA followed by Tukey post-test. Samples denoted letter "a" are statistically different from samples denoted letter "b." Samples denoted letters "ab" are not statistically different from those denoted letter "a" or letter "b."

Example 8

Figure 6:
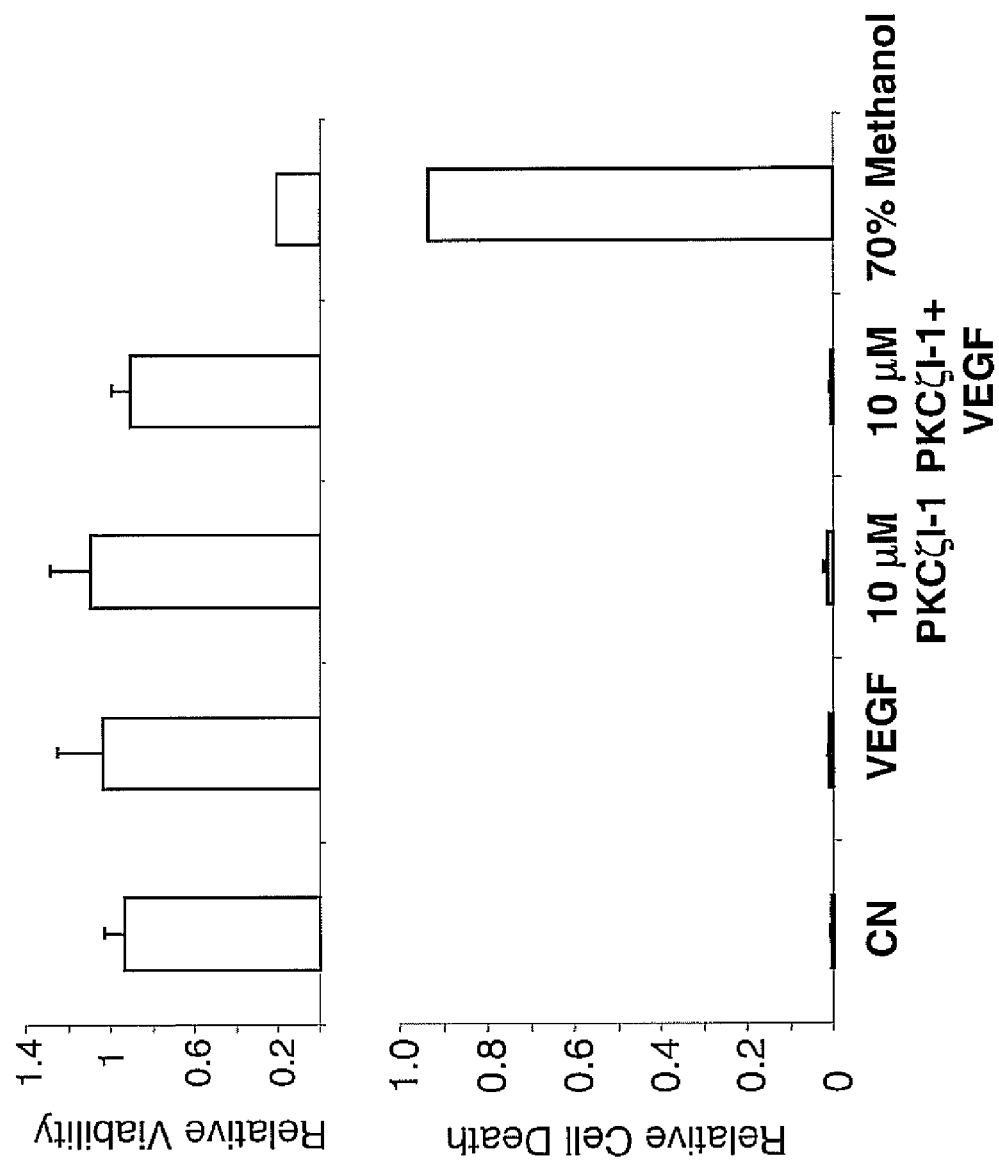
FIG. 6 is a graph showing that PKC-zeta I1 does not alter cell viability or increase cell death.

FIG. 6 shows that PKC-zeta I1 does not alter cell viability or increase cell death. Cell viability is measured using the Invitrogen Live/Dead assay according to manufacturer's instructions. Confluent BREC cultures are treated with 10 micromolar PKC-zeta I1 for 24 h. Cell viability is measured with calcein AM incorporation and cell death is measured by ethidium homodimer-1 staining followed by fluorescence quantification on a Molecular Devices Gemini fluorescence plate reader. After 24 h treatment there is no loss of cell viability and no increase in cell death with PKC-zeta I1 treatment alone or with VEGF compared to control, n=5 for all conditions.

Example 9

In vitro permeability assays demonstrate that cPKC contributes to VEGF induced permeability. Bovine retinal endothelial cells (BREC) are grown to confluence on transwell filters (Costar) and treated with hydrocortisone (100 nM) to induce barrier properties. cPKC inhibitor, bisindoylmaleimide I, 5 micromolar, is applied to the cells 30 min before addition of fluorescent-labeled tracer and VEGF (50 ng/mL, R&D Systems) is applied to the cells for 15 min before addition of tracer. RITC-labeled 70 kDa dextran (Sigma) is used as a tracer for cell permeability measures and is applied to the apical chamber at 10 micromolar. Samples are drawn from the basolateral chamber over a 4 h time course and the rate of tracer accumulation is used to determine monolayer permeability, Po, in cm/s. VEGF stimulated dextran permeability in the endothelial monolayer and inhibition of cPKC partly reduces VEGF stimulated permeability.

Example 10

In vitro permeability assays demonstrate that PKC beta contributes to VEGF induced permeability. Bovine retinal endothelial cells (BREC) are grown to confluence on transwell filters (Costar) and treated with hydrocortisone (100 nM) to induce barrier properties. PKC beta, wild type or mutant dominant negative S217A were transfected into cells using amaxa transfection of plasmid. On the day of the experiment, fluorescent-labeled tracer and VEGF (50 ng/mL, R&D Systems) is applied to the cells for 15 min before addition of tracer RITC-labeled 70 kDa dextran (Sigma) is used as a tracer for cell permeability measures and is applied to the apical chamber at 10 micromolar. Samples are drawn from the basolateral chamber over a 4 h time course and the rate of tracer accumulation is used to determine monolayer permeability, Po, in cm/s. VEGF stimulated dextran permeability in the endothelial monolayer and inhibition of PKC beta partly reduces VEGF stimulated permeability.

Example 11

In vitro Assay for Identification of an Inhibitor for PKC zeta

A screen for PKC zeta inhibitors was developed using recombinant human enzyme from Biomol International (SE-413) and CREBtide (Biomol P195) as the substrate. PKC zeta is incubated for 8 min at 30° C. in 50 microliters of buffer containing 5 mM $MgCl_2$, 100 micromolar $Na_3VO_4$, 100 micromolar $Na_4P_2O_7$, 1 mM NaF, 100 micromolar PMSF, 50 mM Tris (pH 7.5), 4 micrograms of phosphatidylserine, 50 micromolar ATP, and a substrate peptide, KRREILSR-RPSYR. The substrate peptide may be chemically synthesized, recombinantly produced or obtained commercially by the trade name CREBtide. Approximately 9,000 compounds from the DIVERSet collection of the ChemBridge Corporation (San Diego, Calif.) were tested at a final concentration of 100 micromolar, using the Kinase-Glo™ Luminescent Kinase assay (Promega) to measure residual ATP levels after the kinase reaction as described by the manufacturer. Compounds are identified as having inhibitory activity when they reduce PCK zeta activity by at least 50% when tested at a concentration of 100 micromolar.

The compound of formula (III), which inhibits PKC zeta with 1.2-fold greater efficacy than the compound of formula (I) when tested at 100 micromolar. The compound of formula (IV), which inhibits PKC zeta with 1.8-fold greater efficacy than the compound of formula (I) when tested at 100 micromolar. The compound of formula (V), which inhibits PKC zeta with 2.6-fold greater efficacy than the compound of formula (I) when tested at 100 micromolar.

Example 12

In Vivo Assay For PKC zeta Inhibitors

The effect of the PKC zeta inhibitor on PKC zeta activity in vivo is assessed by intraocular delivery of the PKC zeta inhibitor to the retina. Male Sprague-Dawley rats (Charles River Breeding Laboratories) weighings 150 to 175 g (1.5 to 2 months of age) are used in these studies. Rat are used for study of PKC zeta activity after vascular endothelial growth factor (VEGF) injection or VEGF injection plus inhibitor of PKC zeta. All injections are intraocular injections done under anesthesia with ketamine/xylazine anesthesia (40 mg/kg ketamine and 4 mg/kg xylazine, intramuscular or intraperitoneal). Injections are performed after corneal reflex is lost due to anesthesia. A 30 gauge needle is used for the injection of VEGF at 2 ng/eye, which is in phosphate buffered saline in a volume of 5 microliters. Alternatively, the same 5 microliters volume contains VEGF and the myristoylated peptide inhibitor of PKC zeta at 500 nM or the PKC zeta inhibitor of formula (I) at a concentration of 100-500 micromolar. The vitreous volume of the rat is approximately 30-50 microliters yielding an ~10× dilution. The animals are decapitated 15 min after injection for PKC zeta activity measures. Alternatively, the animals are allowed to recover for 4 hours and again be anesthetized (40 mg/kg ketamine and 4 mg/kg xylazine) for Evan's blue permeability assay.

In a further alternative, a PKC zeta inhibitor is injected intraperitoneally twice daily at 10-50 micromoles per Kg in control or diabetic rats. For preventive studies the inhibitor is injected before induction of diabetes and for intervention studies drug is injected 1 month after induction of diabetes. Animals are harvested 3 months after induction of diabetes for measures of PKC zeta activity and permeability assays.

Example 13

Induction of Diabetes Using Streptozotocin

Diabetes is induced in male Sprague-Dawley rats (150-175 g, Charles River) by intraperitoneal injection of streptozotocin (65 mg/ml/kg, in 10 mM citrate buffer, pH4.5). The drug is made up as 65 mg/ml concentration and dose delivered to each animal is adjusted to 65 mg/kg by setting the volume relative to the animal's weight. For example, a 500 g rat is injected with 0.5 ml of the 65 mg/ml solution, delivering a total of 32.5 mg of streptozotocin to the rat, and resulting in a dose of 65 mg/ml/kg. Control rats are injected with buffer only. Diabetes is confirmed three days after streptozotocin injection by measuring blood glucose in a drop of blood from the tail, using a Lifescan (One Touch) glucose monitor. A small puncture is placed close to the tip of the tail with a sharp needle or pointed scalpel and a small drop of blood is exuded from the tail. The procedure causes minimum discomfort to the rat and lasts less than 5 seconds. The tail wound is cleaned with alcohol and heals quickly. Before sacrifice the rats are weighed and anesthetized with sodium pentobarbital (intra-peritoneal injection, 100 mg/kg). When deep anesthesia is obtained (determined by loss of corneal reflex) the rat is decapitated to facilitate collection of blood sample for post-mortem determination of blood glucose and other metabolites, as needed.

Example 14

PKC zeta Activity Assay from Cell or Retinal Lysates

Effects of a PKC zeta inhibitor may be assessed in vitro or in vivo using a PKC zeta activity assay from cell or retinal lysates. Following administration of a PKC zeta inhibitor, PKC zeta is immunoprecipitated from control and treated cell lysates or retinal lysates using PKC zeta antibody (Santa Cruz). Lysates are made with lysis buffer (100 mM NaCl, 1% Triton X-100, 10 mM Hepes (pH7.5), 1 mM $Na_3VO_4$, 10 mM diNaPyrophosphate, 10 mM Benzamidine, 10 mM NaF, complete EDTA-free protease inhibitor tablet (Roche)) and retinas are homogenized with 10×1 sec pulses using a probe sonicator (Tekmar sonic disruptor). Cells are lifted by a cell lifter in lysis buffer. Lysates will be precleared with 60 microliters of sepharose G beads by rocking at 4° C. for 1 h and brief centrifugation. Immunoprecipitation is carried out with 5 microliters of PKC zeta antibody for 4 h followed by 60 microliters of sepharose G beads. Beads are pelleted by brief centrifugation in a microfuge and washed 5× with lysis buffer and twice with reaction buffer (see below). Immunoprecipitated PKC zeta is incubated for 8 min at 30° C. in 50 microliters of reaction buffer containing 5 mM $MgCl_2$, 100 micromolar $Na_3VO_4$, 100 μM $Na_4P_2O_7$, 1 mM NaF, 100 micromolar PMSF, 50 mM Tris (pH 7.5), 4 micrograms of phosphatidylserine, 50 micromolar ATP, 3-5 microCi of [g-$^{32}$P]ATP, and 40 micromolar biotinylated PKC zeta substrate (Quality Controlled Biochemicals). Aliquots of the reaction mixture are then spotted on P81 filter paper, washed with 5% acetic acid, and counted for $^{32}$P radioactivity. Activity is assessed compared to no immunoprecipitating antibody control.

Example 15

In vitro Assay for PKC zeta Activity in Cell Signaling.

Activity of PKC zeta in cell growth in response to growth factor addition is detected using an assay including a PKC zeta inhibitor composition. For example, a PKC zeta inhibitor is used in a cell growth assay in response to growth factor addition. In such an assay, cells in vivo, isolated primary cells or cells of a transformed cell line are treated with a growth factor and incorporation of radiolabeled thymidine (tritiated-thymidine) is measured to assess DNA replication. DNA precipitates are quantitated for incorporation of radiolabeled thymidine into DNA using a radio-isotope counter. Cells are pretreated with PKC zeta inhibitor to prevent signal transduction through PKC zeta and the ability of growth factor to stimulate DNA synthesis is quantitated and compared to untreated control cells.

Example 16

In vitro Assay for PKC zeta Activity in Cell Signaling.

Glucose uptake into a cell in response to insulin is measured to determine the role of PKC zeta in insulin signal transduction. Insulin responsive cells, such as isolated pancreatic beta cells or an insulin-responsive cell line are treated with insulin and provided radio-labeled 2-deoxy-glucose, a non-metabolizable form of glucose. Cells are pre-treated with PKCzeta inhibitor and the effect of insulin on glucose uptake compared to controls by quantitation of 2-deoxyglucose uptake.

Any patents or publications mentioned in this specification are incorporated herein by reference to the same extent as if each individual publication is specifically and individually indicated to be incorporated by reference. In particular, U.S. Provisional Patent Application Ser. No. 60/832,362, filed Jul. 21, 2006, is hereby incorporated by reference in its entirety.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

Having described our invention, we claim:

1. A method of treating a disease or disorder in a subject, the disease or disorder characterized by abnormal permeability of vascular tight junctions, comprising:
administering a composition comprising a therapeutically effective amount of a protein kinase C zeta inhibitor, wherein the protein kinase C zeta inhibitor is selected from the group consisting of:

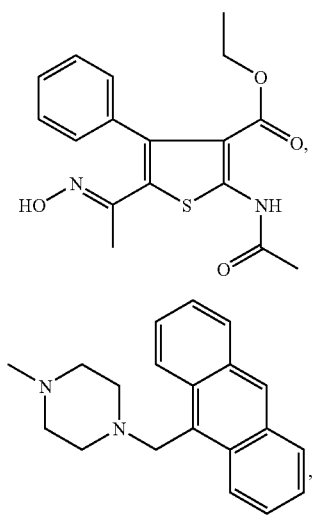
(I)

(II)

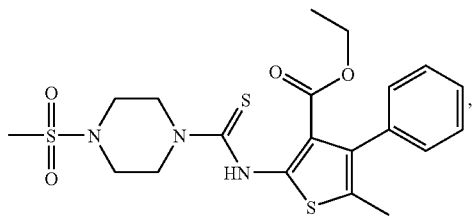
(III)

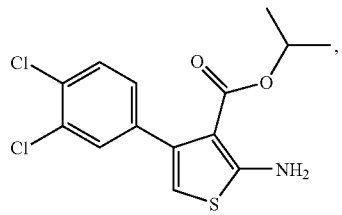
(IV)

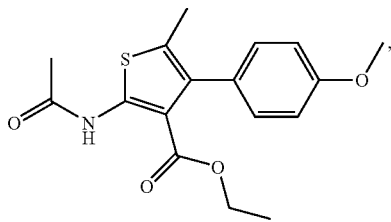
(V)

and a pharmaceutically acceptable salt or hydrate thereof.

* * * * *

UNITED STATES PATENT AND TRADEMARK OFFICE
CERTIFICATE OF CORRECTION

PATENT NO. : 7,585,865 B2
APPLICATION NO. : 11/781498
DATED : September 8, 2009
INVENTOR(S) : David A. Antonetti et al.

It is certified that error appears in the above-identified patent and that said Letters Patent is hereby corrected as shown below:

Column 1, lines 13-16 - Replace "The subject matter of this application was researched by the National Institute of Health under Contract No. EY016413. Accordingly, the United States government may have certain rights in this invention."

with --This invention was made with government support under Contract Nos. EY012021 and EY016413 awarded by the National Institutes of Health. The government has certain rights in this invention.--

Column 32, line 32 - Add claims 29-31:

--29. The method of claim 28 wherein the administering comprises administration by a systemic route.

30. The method of claim 28 wherein the administering comprises administration by a local route.

31. The method of claim 28 further comprising administering an antineoplastic therapeutic agent.--

Signed and Sealed this

Sixth Day of April, 2010

David J. Kappos
*Director of the United States Patent and Trademark Office*